(12) United States Patent
Takeda

(10) Patent No.: US 10,631,820 B2
(45) Date of Patent: Apr. 28, 2020

(54) ULTRASOUND DIAGNOSTIC IMAGING APPARATUS AND ULTRASOUND IMAGE DISPLAY METHOD

(71) Applicant: Konica Minolta, Inc., Tokyo (JP)

(72) Inventor: Yoshihiro Takeda, Hino (JP)

(73) Assignee: KONICA MINOLTA, INC., Tokyo (JP)

(*) Notice: Subject to any disclaimer, the term of this patent is extended or adjusted under 35 U.S.C. 154(b) by 1331 days.

(21) Appl. No.: 14/258,380

(22) Filed: Apr. 22, 2014

(65) Prior Publication Data

US 2014/0323854 A1    Oct. 30, 2014

(30) Foreign Application Priority Data

Apr. 25, 2013  (JP) ................................. 2013-092228

(51) Int. Cl.
*A61B 8/08*    (2006.01)
*G01S 15/89*   (2006.01)
(Continued)

(52) U.S. Cl.
CPC .......... *A61B 8/0841* (2013.01); *A61B 8/0833* (2013.01); *A61B 8/461* (2013.01);
(Continued)

(58) Field of Classification Search
CPC ..... A61B 34/20; A61B 8/463; A61B 17/3403; A61B 2017/00075; A61B 2017/3413;
(Continued)

(56) References Cited

U.S. PATENT DOCUMENTS 5,810,008 A * 9/1998 Dekel ...................... A61B 8/00
                                                    128/916
6,336,899 B1   1/2002 Yamazaki
(Continued)

FOREIGN PATENT DOCUMENTS

JP    2001-269339    10/2001
JP    2003-116855    4/2003
(Continued)

OTHER PUBLICATIONS

Dehghan et al. "Needle-tissue interaction modeling using ultrasound-based motion estimation: Phantom study." Computer Aided Surgery 13:5, 265-280. (Year: 2008).*
(Continued)

*Primary Examiner* — Amanda Lauritzen Moher
(74) *Attorney, Agent, or Firm* — Lucas & Mercanti, LLP

(57) ABSTRACT

Disclosed is an ultrasound diagnostic imaging apparatus including an ultrasound probe which outputs transmission ultrasound to a subject according to a drive signal, a puncture needle being inserted in the subject, and which outputs a received signal obtained by receiving reflected ultrasound from the subject. The ultrasound diagnostic imaging apparatus further includes an image generation unit which generates ultrasound image data for each frame, a display unit which displays an ultrasound image, an evaluation information generation unit which generates movement evaluation information indicating movement evaluation between frames, a puncture needle position detection unit which detects a position of a tip of the puncture needle on a basis of the movement evaluation information, a highlighting unit which highlights display of a tip image in the ultrasound image and a speed calculation unit which calculates moving speed of the tip of the puncture needle.

14 Claims, 15 Drawing Sheets

(51) Int. Cl.
*A61B 8/00* (2006.01)
*G06T 7/00* (2017.01)
*G06T 7/20* (2017.01)
*A61B 17/34* (2006.01)
*A61B 34/20* (2016.01)
*G06T 7/73* (2017.01)
*A61B 8/14* (2006.01)
*G06T 11/00* (2006.01)
*A61B 10/02* (2006.01)
*A61B 5/06* (2006.01)
*A61B 17/00* (2006.01)
*A61B 90/00* (2016.01)

(52) U.S. Cl.
CPC ............ *A61B 8/463* (2013.01); *A61B 8/5207* (2013.01); *A61B 8/5215* (2013.01); *A61B 17/3403* (2013.01); *A61B 34/20* (2016.02); *G01S 15/89* (2013.01); *G06T 7/0012* (2013.01); *G06T 7/20* (2013.01); *G06T 7/73* (2017.01); *A61B 5/06* (2013.01); *A61B 5/061* (2013.01); *A61B 8/14* (2013.01); *A61B 8/4405* (2013.01); *A61B 8/4444* (2013.01); *A61B 10/02* (2013.01); *A61B 2017/00075* (2013.01); *A61B 2017/3413* (2013.01); *A61B 2034/2065* (2016.02); *A61B 2090/378* (2016.02); *G01S 15/8915* (2013.01); *G06T 11/00* (2013.01); *G06T 2207/10132* (2013.01); *G06T 2207/30021* (2013.01); *G06T 2207/30241* (2013.01)

(58) Field of Classification Search
CPC ...... A61B 2034/2065; A61B 2090/378; A61B 8/0841; A61B 8/4405; A61B 8/5207; A61B 8/5215; A61B 10/02; A61B 5/06; A61B 5/061; A61B 8/0833; A61B 8/14; A61B 8/4444; A61B 8/461; G06T 2207/10132; G06T 2207/30021; G06T 2207/30241; G06T 7/73; G06T 11/00; G06T 7/0012; G06T 7/20; G01S 15/89; G01S 15/8915
See application file for complete search history.

(56) References Cited

U.S. PATENT DOCUMENTS

| | | | | |
|---|---|---|---|---|
| 2001/0036245 | A1* | 11/2001 | Kienzle, III | A61B 6/12 378/4 |
| 2010/0228238 | A1* | 9/2010 | Brennan | A61B 5/0066 606/13 |
| 2011/0150280 | A1* | 6/2011 | Tsuji | G06T 7/248 382/103 |
| 2012/0078103 | A1* | 3/2012 | Tashiro | A61B 8/0841 600/443 |
| 2014/0187942 | A1* | 7/2014 | Wang | A61B 8/0841 600/439 |
| 2014/0275985 | A1* | 9/2014 | Walker | A61B 5/062 600/424 |
| 2015/0342561 | A1* | 12/2015 | Takeda | A61B 8/0841 600/424 |

FOREIGN PATENT DOCUMENTS

| | | |
|---|---|---|
| JP | 2006-263386 | 10/2006 |
| JP | 2012070837 A | 4/2012 |
| JP | 2012-120747 A | 6/2012 |
| JP | 2012120747 A | 6/2012 |

OTHER PUBLICATIONS

Notification of Reasons for Refusal dated Aug. 30, 2016 from corresponding Japanese application; Patent Application No. 2013-092228; English translation of Notification of Reasons for Refusal; Total of 12 pages.
European Search Report EP 14 16 5727, dated Jul. 17, 2014 (8 pages).

\* cited by examiner

ULTRASOUND DIAGNOSTIC IMAGING APPARATUS AND ULTRASOUND IMAGE DISPLAY METHOD

BACKGROUND OF THE INVENTION

1. Field of the Invention

The present invention relates to an ultrasound diagnostic imaging apparatus and an ultrasound image display method.

2. Description of Related Art

Biopsy where a puncture needle is inserted in a living body and where a piece of tissue or body fluid is obtained to make diagnosis has been performed. Here, in order not to insert the puncture needle at a different position in the living body by mistake when obtaining a predetermined tissue or the like, the puncture needle is to be attached to an ultrasound probe provided with an attachment or a guide, and an operator such as a physician makes an ultrasound image be displayed according to ultrasound image data of inside the living body obtained by the ultrasound probe and performs inserting of the puncture needle while confirming the inserting position by looking at the display.

When performing insertion, in order to surely bring the puncture needle to the target part, an operator inserts the puncture needle following a predetermined inserting path by looking at an ultrasound image.

When performing such paracentesis, it is important that the puncture needle, especially the tin portion thereof, can be surely and appropriately confirmed on a monitor because the puncture needle needs to be brought to the target position to drain excess liquid or to perform clysis.

In view of the above, there is known a conventional ultrasound diagnostic imaging apparatus which generates differential echo signals between time series frames based on echo signals of a plurality of time series frames, detects a candidate for the tip of the puncture needle based on the generated differential echo signals and displays the part which is the candidate for the tip in a highlighted manner. Such apparatus is disclosed in JP2012-120747, for example. Further, in such ultrasound diagnostic imaging apparatus, narrowing down within a plurality of candidates for the tip is performed on the basis of the candidates for the tip which are detected in the past.

SUMMARY OF THE INVENTION

An operator performs insertion of a puncture needle while confirming the position of the puncture needle in an ultrasound image. However, since insertion speed of the puncture needle varies and depends on the ability and condition of the operator, how much the puncture needle will proceed cannot be predicted in a method where the tip position of the puncture needle is specified based only on the candidates for the tip which are detected in the past as described in JP 2012-120747. Therefore, it is difficult to determine which one of the plurality of candidates for the tip is the true position of the tip of the puncture needle, and the tip position of the puncture needle in the ultrasound image cannot be fully recognized.

In view of the above, an object of the present invention is to provide an ultrasound diagnostic imaging apparatus and an ultrasound image display method which can more accurately recognize the tip position of a puncture needle.

In order to realize at least one object, an ultrasound diagnostic imaging apparatus reflecting one aspect of the present invention includes an ultrasound probe which outputs transmission ultrasound to a subject according to a drive signal, a puncture needle being inserted in the subject, and which outputs a received signal obtained by receiving reflected ultrasound from the subject, an image generation unit which generates ultrasound image data for each frame on a basis of the received signal output from the ultrasound probe, a display unit which displays an ultrasound image on a basis of the ultrasound image data generated by the image generation unit, an evaluation information generation unit which generates movement evaluation information indicating movement evaluation between frames on a basis of ultrasound image data of a plurality of frames, a puncture needle position detection unit which detects a position of a tip of the puncture needle on a basis of the movement evaluation information generated by the evaluation information generation unit, a highlighting unit which highlights display of a tip image in the ultrasound image, the tip image corresponding to the position of the tip of the puncture needle detected by the puncture needle position detection unit, and a speed calculation unit which calculates moving speed of the tip of the puncture needle, and the puncture needle position detection unit detects the position of the tip of the puncture needle on a basis of the moving speed of the tip of the puncture needle obtained by the speed calculation unit.

Preferably, the speed calculation unit calculates acceleration of the tip of she puncture needle, and the puncture needle position detection unit detects the position of the tip of the puncture needle on a basis of the moving speed and the acceleration of the tip of the puncture needle obtained by the speed calculation unit.

Preferably, the ultrasound diagnostic imaging apparatus further includes a history storage unit wherein history information relating to the position on of the tip of the puncture needle detected by the puncture needle position detection unit is stored, and the speed calculation unit calculated moving speed of the tip of the puncture needle on a basis of the history information relating to the position of the tip of the puncture needle stored in the history storage unit.

Preferably, the evaluation information generation unit generates the movement evaluation information by obtaining differential signals between the ultrasound image data of the plurality of frames.

Preferably, the evaluation information generation unit calculates correlation coefficients between the ultrasound image data of the plurality of frames with respect to individual pixels and generates the movement evaluation information by obtaining a signal expressing the calculated correlation coefficients of the individual pixels.

Preferably, the evaluation information generation unit generates the movement evaluation information by analyzing time direction variance between the ultrasound image data of the plurality of frames with respect to individual pixels.

Preferably, the puncture needle position detection unit detects a position of the tip of the puncture needle within a predetermined range from the position of the tip of the puncture needle detected in a frame which is one frame before.

Preferably, the puncture needle position detection unit obtains a straight line trajectory of the tip of the puncture needle on a basis of position history of the tip of the puncture needle and detects the position of the tip of the puncture needle at a periphery of the straight line trajectory.

Preferably, the puncture needle position detection unit detects the position on of the tip of the puncture needle on a basis of the movement evaluation information generated by the evaluation information generation unit by using a particle filter.

Preferably, the highlighting unit highlights the display of the tip image by increasing brightness of the tip image.

Preferably, the highlighting unit highlights the display of the tip image by changing a display color of the tip image.

Preferably, the ultrasound diagnostic imaging apparatus further includes a trajectory display unit which displays a trajectory of the tip of the puncture needle on a basis of position history of the tip of the puncture needle.

Preferably, the trajectory display unit obtains a least squares line on a basis of the position history of the tip of the puncture needle and displays the trajectory of the tip of the puncture needle on a basis of the least squares line.

In order to realize at least one object, an ultrasound diagnostic imaging apparatus reflecting another aspect of the present invention includes an ultrasound probe which outputs transmission ultrasound to a subject according to a drive signal, a puncture needle being inserted in the subject, and which outputs a received signal obtained by receiving reflected ultrasound from the subject, an image generation unit which generates ultrasound image data for each frame on a basis of the received signal output from the ultrasound probe, a display unit which displays an ultrasound image on a basis of the ultrasound image data generated by the image generation unit, a target image deciding unit which performs global matching between individual ultrasound image data of a plurality of frames and ultrasound image data of a newest frame to obtain correlations of the individual ultrasound image data of the plurality of frames to the ultrasound image data of the newest frame and decides ultrasound image data whose correlation equals to or is greater than a predetermined threshold and which is oldest in terms of time as a target image data, an evaluation information generation unit which generates movement evaluation information indicating movement evaluation between frames on a basis of the target image data decided by the target image deciding unit and the ultrasound image data of the newest frame, a puncture needle position detection unit which detects a position of a tip of the puncture needle on a basis of the movement evaluation information generated by the evaluation information generation unit, and a highlighting unit which highlights display of a tip image in the ultrasound image, the tip image corresponding to the position of the tip of the puncture needle detected by the puncture needle position detection unit.

In order to realize at least one object, an ultrasound diagnostic imaging apparatus reflecting another aspect of the present invention includes an ultrasound probe which outputs transmission ultrasound to a subject according to a drive signal, a puncture needle being inserted in the subject, and which outputs a received signal obtained by receiving reflected ultrasound from the subject, an image generation unit which generates ultrasound image data for each frame on a basis of the received signal output from the ultrasound probe, a display unit which displays an ultrasound image on a basis of the ultrasound image data generated by the image generation unit, an evaluation information generation unit which generates movement evaluation information indicating movement evaluation between frames on a basis of ultrasound image data of a plurality of frames, a puncture needle position detection unit which detects a position of a tip of the puncture needle on a basis of the movement evaluation information generated by the evaluation information generation unit, and a highlighting unit which highlights display of a tip image in the ultrasound image, the tip image corresponding to the position of the tip of the puncture needle detected by the puncture needle position detection unit, and the evaluation information generation unit generates the movement evaluation information by analyzing time direction variance between the ultrasound image data of the plurality of frames with respect to individual pixels.

In order to realize at least one object, an ultrasound image display method reflecting one aspect of the present invention includes first generating ultrasound image data on a basis of a received signal output from an ultrasound probe which outputs transmission ultrasound to a subject according to a drive signal, a puncture needle being inserted in the subject, and outputs the received signal obtained by receiving reflected ultrasound from the subject, displaying an ultrasound image on a basis of the ultrasound image data generated in the first generating, second generating movement evaluation information which indicates movement evaluation between frames on a basis of ultrasound image data of a plurality of frames in time series, detecting a position of a tip of the puncture needle on a basis of the movement evaluation information generated in the second generating, highlighting display of a tip image in the ultrasound image, the tip image corresponding to the position of the tip of the puncture needle detected in the detecting, and calculating moving speed of the tip of the puncture needle, and in she detecting, the position of the tip of the puncture needle is detected on a basis of the moving speed of the tip of the puncture needle obtained in the calculating.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Figure 1:
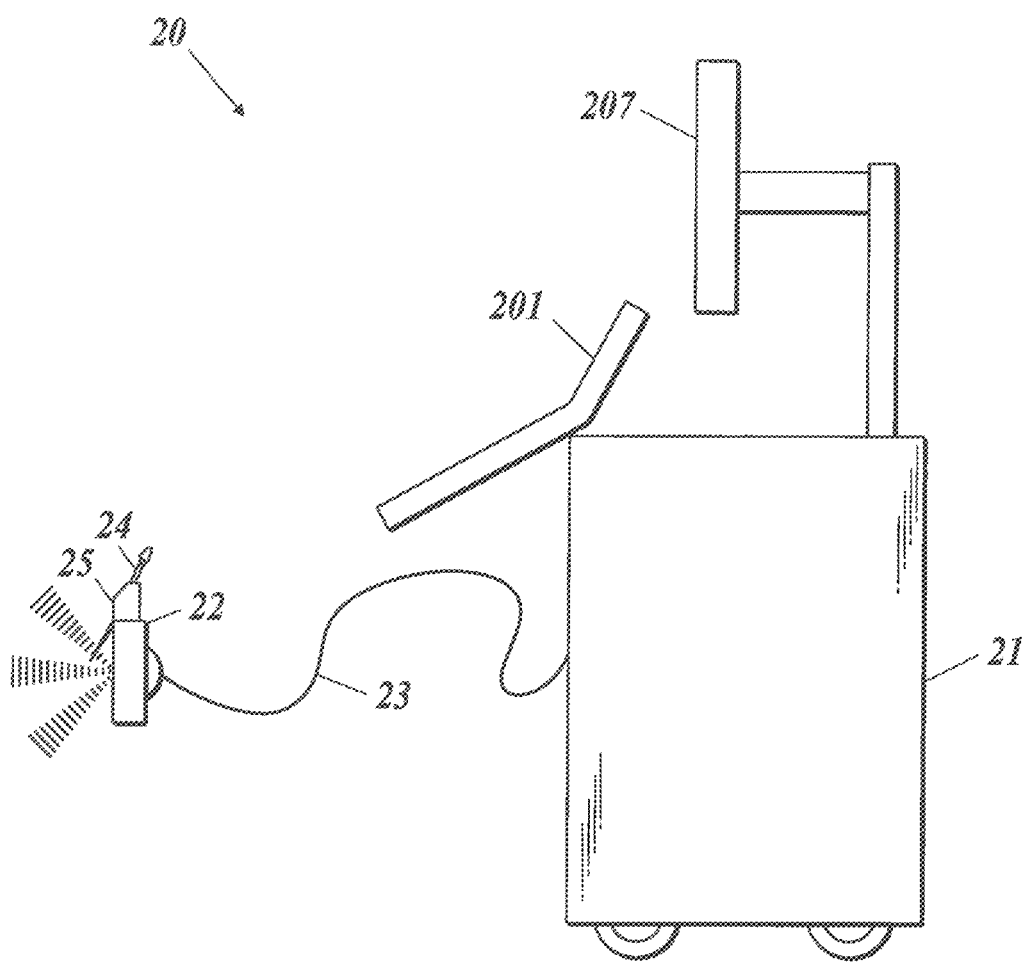
FIG. 1 is a drawing showing an outer structure of an ultrasound diagnostic imaging apparatus.

Hereinafter, the ultrasound diagnostic imaging apparatus according to an embodiment of the present invention will be described with reference to the drawings. However, the scope of the invention is not limited to the examples shown in the drawings. In the following description, the same reference numerals are used for components having the same functions and configurations, and their descriptions are omitted.

Figure 2:
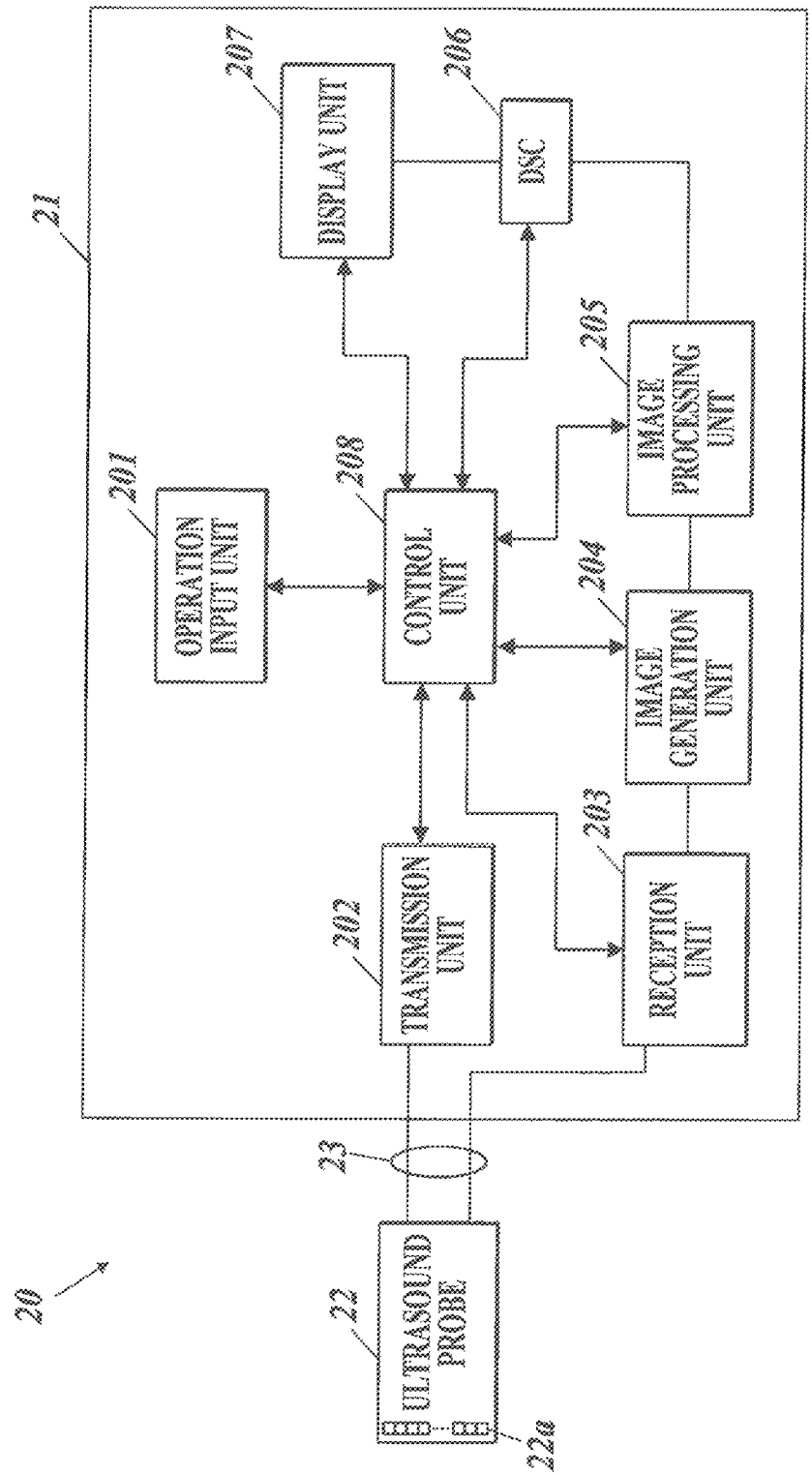
FIG. 2 is a block diagram showing a schematic configuration of the ultrasound diagnostic imaging apparatus.

As shown in FIGS. 1 and 2, the ultrasound diagnostic imaging apparatus 20 according to an embodiment includes an ultrasound diagnostic imaging apparatus main body 21 and an ultrasound probe 22. The ultrasound probe 22 transmits ultrasound (transmission ultrasound) to a subject such as a living body (not shown in the drawing) and receives reflected wave (reflected ultrasound: echo) of the ultrasound reflected off the subject. The ultrasound diagnostic imaging apparatus main body 21 is connected with the ultrasound probe 22 via a cable 23. The ultrasound diagnostic imaging apparatus main body 21 transmits drive signals which are electric signals to the ultrasound probe 22 to make the ultrasound probe 22 transmit transmission ultrasound to a subject and visualizes the inside state of the subject as an ultrasound image on the basis of the received signals which are electric signals generated in the ultrasound probe 22 according to the reflected ultrasound from, inside of the subject received by the ultrasound probe 22.

The ultrasound probe 22 includes transducers 22a formed of piezoelectric elements and for example, the transducers 22a are aligned in a one-dimensional array in an orientation direction. In the embodiment, for example, an ultrasound probe 22 provided with 192 transducers 22a is used. Here, the transducers 22a may be aligned in a two-dimensional array. Further, the number of transducers 22a can be set arbitrarily. Although a linear scanning type electronic-scanning probe is used as the ultrasound probe 22 in the embodiment, either an electronic-scanning type or a mechanic-scanning type can be used. Further, any type of linear scanning, sector scanning and convex scanning can be adopted.

Further, on a side of the ultrasound probe 22, an attachment 25 which guides insertion of a puncture needle 24 into a subject in an orientation direction is provided. The attachment 25 guides the puncture needle 24 to be inserted so that the inserting angle is specified and the attachment 25 can change the inserting angle.

In the embodiment, instead of the attachment 25, a guide groove which provides the ultrasound probe 22 with a guide regarding the inserting angle of the puncture needle 24 may be provided.

As shown in FIG. 2, the ultrasound diagnostic imaging apparatus main body 21 includes an operation input unit. 201, a transmission unit 202, a reception unit 203, an image generation unit 204, an image processing unit 205, a DSC (Digital Scan Converter) 206, a display unit 207 and a control unit 208, for example.

The operation input unit 201 includes various types of switches, buttons, a track ball, a mouse, a key board and the like for inputting commands for instructing the start of diagnosis and data such as personal information relating to a subject, etc. and the operation input unit 201 outputs operation signals to the control unit 208.

The transmission unit 202 is a circuit for supplying drive signals which are electric signals to the ultrasound probe 22 via the cable 23 according to the control of the control unit 208 to make the ultrasound probe 22 generate transmission ultrasound. Further, the transmission unit 202 includes a clock generator circuit, a delay circuit and a pulse generator circuit, for example. The clock generator circuit is a circuit for generating a clock signal for deciding the transmission timing and the transmission frequency of a drive signal. The delay circuit is a circuit for setting delay times in transmission timings of drive signals for individual paths corresponding to the transducers 22a and delays the transmission of the drive signals for the set delay times to concentrate the transmission beams constituted of transmission ultrasound. The pulse generator circuit is a circuit for generating a pulse signal as a drive signal in a predetermined cycle.

The transmission unit 202 configured as described above sequentially switches the transducers 22a to which drive signals are supplied among the plurality of transducers 2a by a predetermined number of transducers 22a for every transmission and reception of ultrasound according to the control of the control unit 208 and supplies drive signals to the selected plurality of transducers 22a to perform scanning.

The reception unit 203 is a circuit for receiving received signals which are electric signals from the ultrasound probe 22 via the cable 23 in compliance with the control of the control unit 208. The reception unit 203 is provided with an amplifier, an A/D conversion circuit and a phasing addition circuit, for example. The amplifier is a circuit for amplifying the received signals at a preset amplification factor for the individual paths corresponding to the transducers 22a. The A/D conversion circuit is a circuit for performing analog/digital conversion (A/D conversion) on the amplified received signals. The phasing addition circuit is a circuit for adjusting time phases of the received signals to which A/D conversion is performed by applying the delay times to the individual paths respectively corresponding to the transducers 22a and generating sound ray data by adding the adjusted received signals (phase addition).

The image generation unit 204 generates B-mode image data by performing envelope detection, logarithmic amplification and the like on the sound ray data from the reception unit 203 and performing brightness conversion by performing gain adjustment and the like. In other words, B-mode image data is data where intensities of received signals are expressed in terms of brightness. The B-mode image data which is generated in the image generation unit 204 is transmitted to the image processing unit 205.

The image processing unit 205 stores B-mode image data output from the image generation unit 204 in the image memory unit 205a (see FIG. 3) in frame units. The image data in frame units may be called ultrasound image data or frame image data. The image processing unit 205 arbitrarily reads out the ultrasound image data stored in the image memory unit 205a and outputs the ultrasound image data to the DSC 206.

Figure 3:
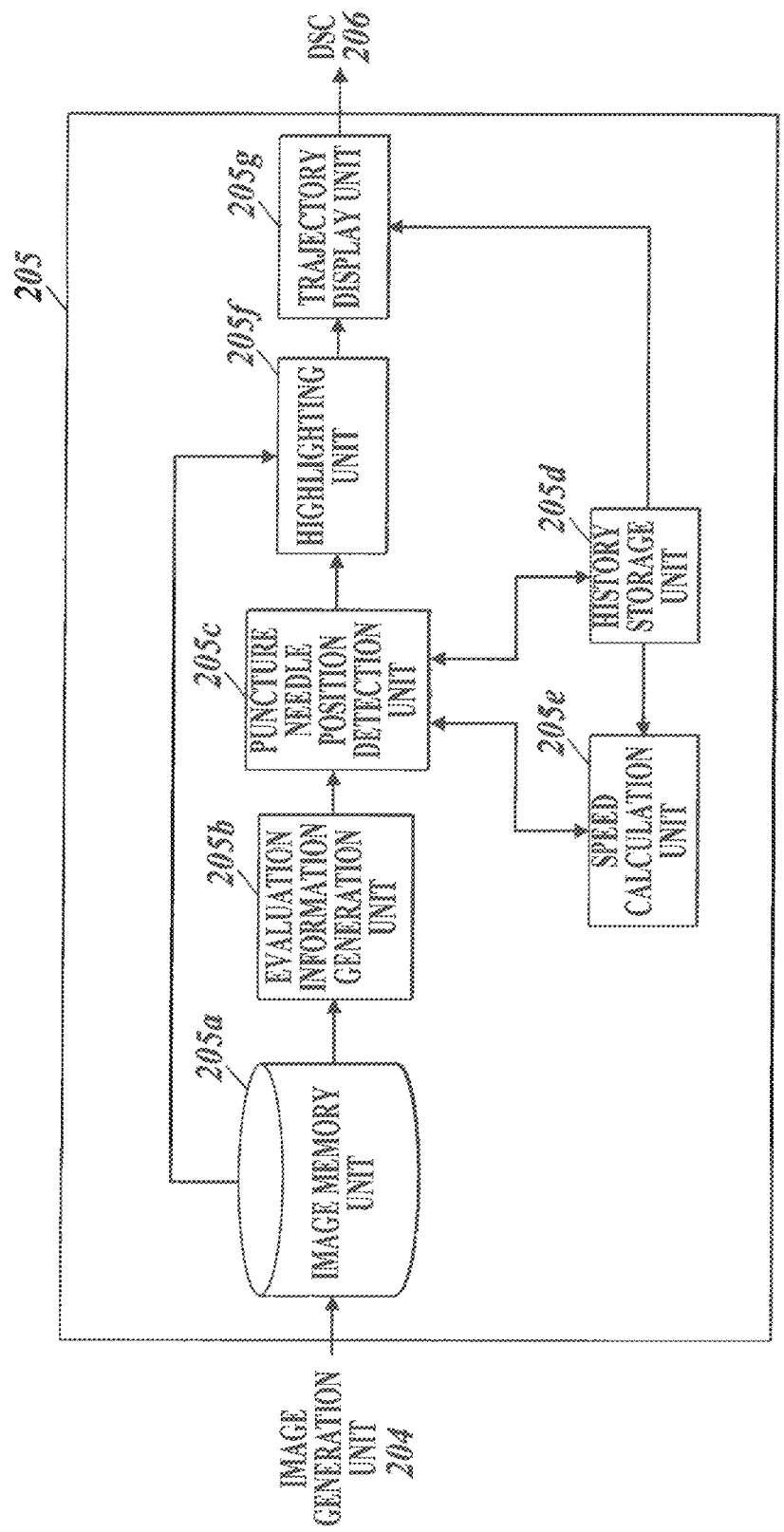
FIG. 3 is a block diagram showing a functional configuration of an image processing unit.

As shown in FIG. 3, the image processing unit 205 includes the image memory unit 205a, an evaluation information generation unit 205b, a puncture needle position detection unit 205c, a history storage unit 205d, a speed calculation unit 205e, a highlighting unit 205f and a trajectory display unit 205g.

The image memory unit 205a is configured with a semiconductor memory such as a DRAM (Dynamic Random Access Memory). The image memory unit 205a is configured to have a great capacity where ultrasound image data of about 10 seconds can be stored, and for example, ultrasound image data of the most recent 10 seconds can be stored in FIFO (First-In First-Out) method.

The evaluation information generation unit 205b generates movement evaluation information between frames using ultrasound image data of a plurality of frames. As for the generation method of movement evaluation information, for example, any of the methods described later can be applied. When generating movement evaluation information, a body movement correction process may be performed by obtaining correlations between ultrasound image data of a plurality of frames to detect misalignment in images and by correcting such misalignment.

[Generation Method of Movement Evaluation Information Using Differential Signals]

Figure 4:
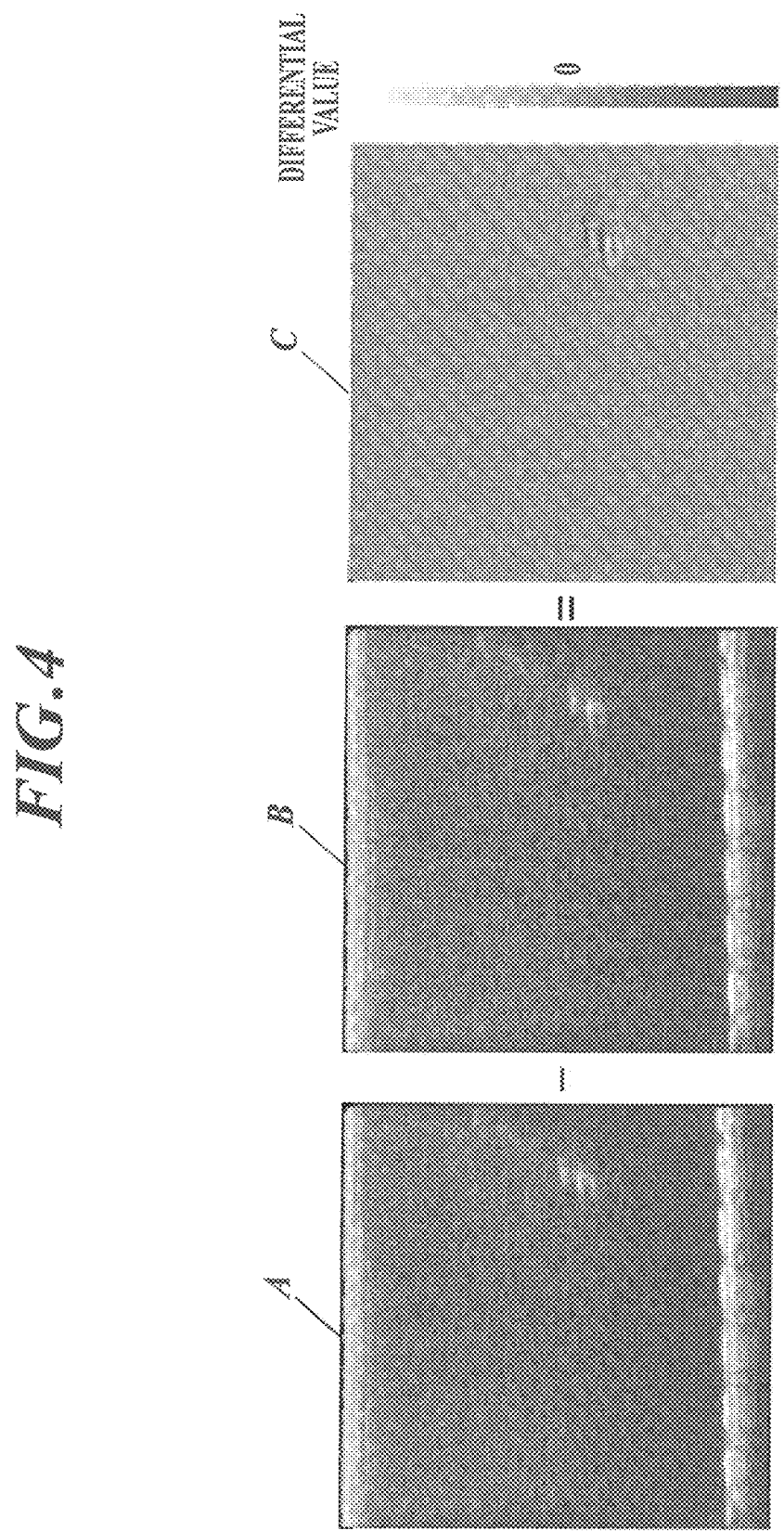
FIG. 4 is a drawing for explaining a generation method of movement evaluation information based on differential signals.

The example shown in FIG. 4 is generation of movement evaluation information performed by obtaining differential signals between ultrasound image data of a plurality of frames.

In particular, the differential signal C which expresses the difference between the pixels of the ultrasound image A which is the newest frame and the pixels of the ultrasound image B which is one frame before the ultrasound image A is obtained. This differential signal C is the movement evaluation information. With respect to the differential signal C, the smaller the absolute value of the difference between the pixel values of the frames, the closer its value is to 0. That is, it can be evaluated that the further the value of the differential signal is from 0, the greater the movement.

[Generation Method of Movement Evaluation Information Using Correlation Coefficients]

Figure 5:
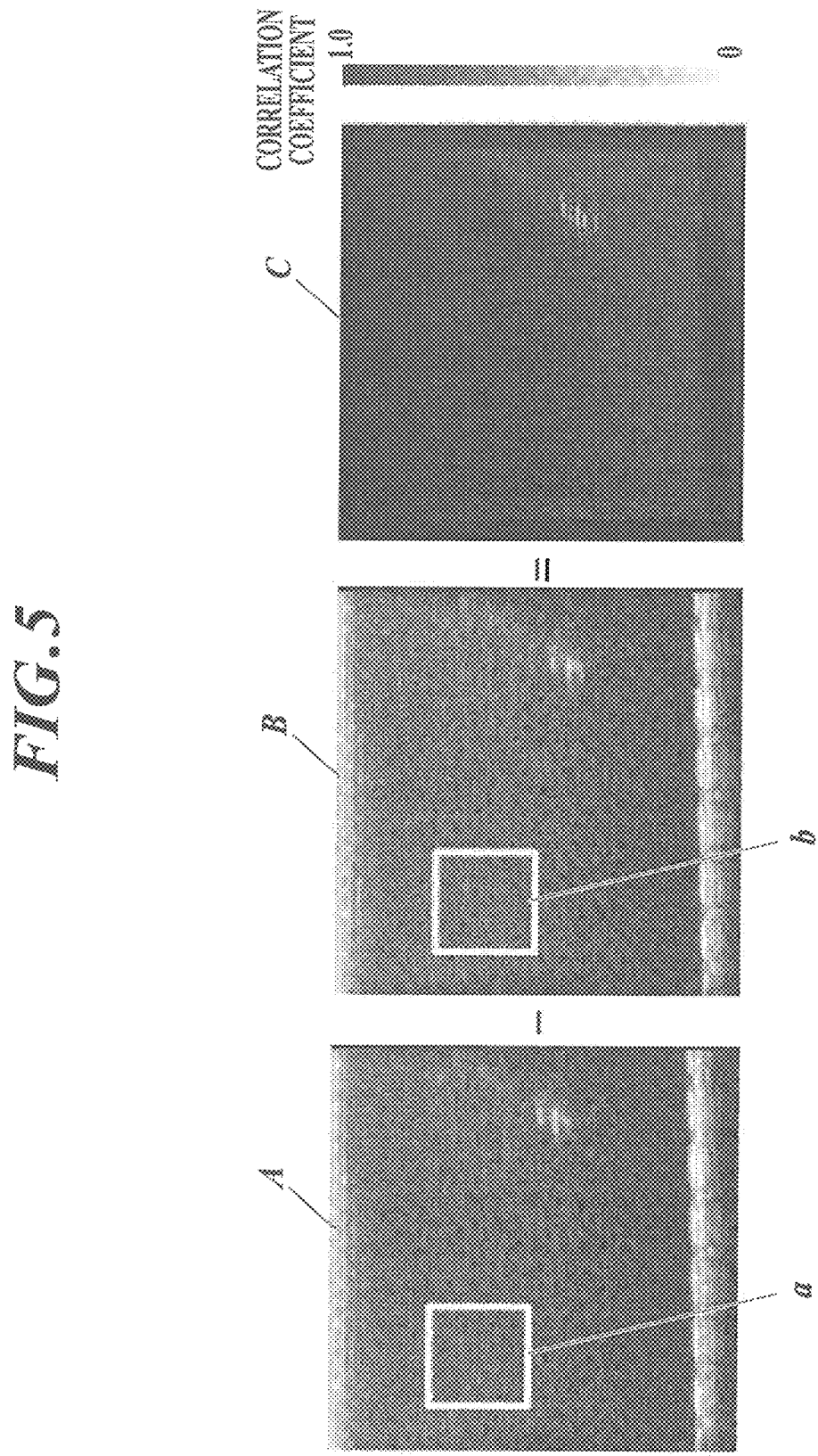
FIG. 5 is a drawing for explaining a generation method of movement evaluation information based on correlation coefficients.

The example shown in FIG. 5 is generation of movement evaluation information by obtaining correlation coefficients between ultrasound image data of a plurality of frames with respect to individual, pixels.

In particular, the area of interest "a" having a predetermined size, the focus pixel (x, y, t) in the ultrasound image A which is the newest frame being the center, is set and the area of interest "b" having a predetermined size, the focus pixel (x, y, t−1) in the ultrasound image B which is one frame before the newest frame, is set. Then, by the following formula (1), the correlation coefficient E (x, y, t) with respect to the focus pixel (x, y) between the ultrasound images A and B is obtained. In the formula (1) below, (i, j) indicate the coordinates of a pixel in an area of interest.

$$E(x, y, t) = \frac{\sum \sum (I(i, j, t) = \bar{I}(t))(I(i, j, t-1) - \bar{I}(t-1))}{\sqrt{\sum \sum (I(i, j, t) - \bar{I}(t))} \sqrt{\sum \sum (I(i, j, t-1) - \bar{I}(t-1))}} \quad \text{[formula 1]}$$

The correlation coefficient E (x, y, t) is a value between 0 and 1.0. That is, it can be evaluated that the smaller the correlation with respect a pixel between frames, the greater the movement. The correlation coefficient E (x, y, t) is obtained for each pixel. The correlation coefficient information D which is generated in such way is the movement evaluation information.

[Generation Method of Movement Evaluation Information Using Time Direction Variance]

Figure 6:
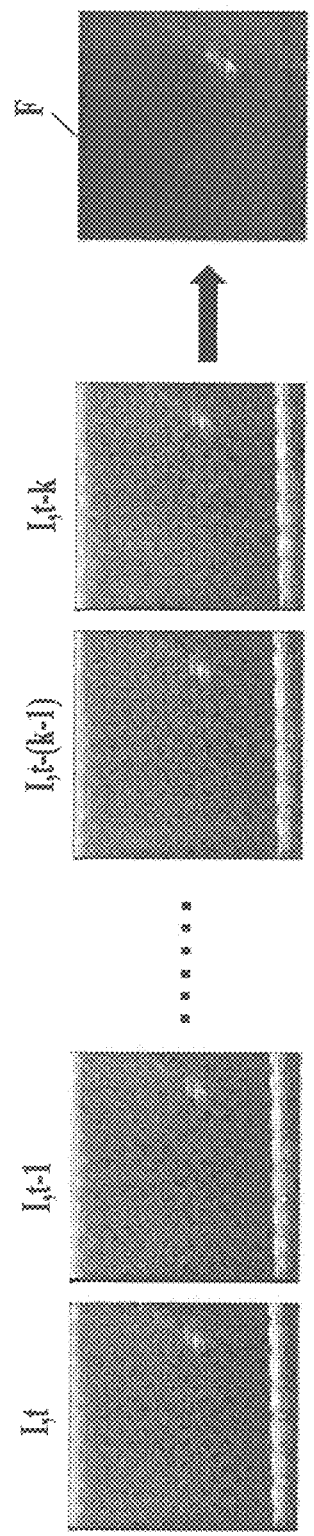
FIG. 6 is a drawing for explaining a generation method of movement evaluation information based on time direction variance.

The example shown in FIG. 6 is generation of movement evaluation information by analyzing time direction variance of pixels between ultrasound image data of a plurality of frames.

In particular, with respect to the ultrasound image data I(t) of the newest frame, the ultrasound image data I(t−1) of the frame which is one frame before the newest frame, . . . , the ultrasound image data I(t−(k−1)) of she frame which is (k−1) frames before the newest frame and the ultrasound image data I(t−k) of the frame which is k frames before the newest frame, variance of pixel value is obtained for individual pixels. For example, with respect to the ultrasound image data of each frame, the pixel value of a certain coordinates (x, y) is extracted. Then, the average, of the extracted pixel values is obtained. Thereafter, with respect to the pixel at the coordinates (x, y) in the ultrasound image data of each frame, its deviation from the average is obtained by the sum of squares. Then, the total sum of the obtained deviations is calculated to obtain the time direction variance value. An value (for example, a standard deviation) which is decided unambiguously when the time direction variance value is decided, such as a value obtained by performing an additional operation on the time direction variance value, may be used as the movement evaluation information. The greater the change in pixel values from the ultrasound image data I(t−k) of the frame which is k frames before the newest frame through the ultrasound image data I(t) of the newest frame, the greater the time direction variance value. The time direction variance value is obtained for each pixel. The time direction variance information F generated as described above is the movement evaluation information. Further, the greater the movement, the greater the range of high time direction variance value. Therefore, the inserting speed of the puncture needle 24 can be recognized easily and the movement of the puncture needle 24 can be predicted easily.

In such method, upon analyzing the time direction variance, the number of ultrasound image data (the number of frames) to be used can be set arbitrarily. However, the greater the number of frames, the more enhanced the detection sensitivity of the puncture needle 24 can be.

The number of frames can be set according to frame rate. In particular, the number of frames FN can be decided as shown in the formula (2) below, for example. In the formula (2) below, FPS indicates frame rate and FNB indicates the number of ultrasound image data to be used in analyzing time direction variance when frame rate is 30 [fps].

$$FN=FPS/30*FNB \quad (2)$$

Therefore, since the difference in the ultrasound image data between frames is small in a case where the frame rate is high, detection accuracy of the tip of the puncture needle 24 can be enhanced by using ultrasound image data of large number of frames. On the other hand, since the difference in the ultrasound image data between frames is great in a case where the frame rate is low, the processing speed can be enhanced by using ultrasound image data of small number of frames.

Figure 7:
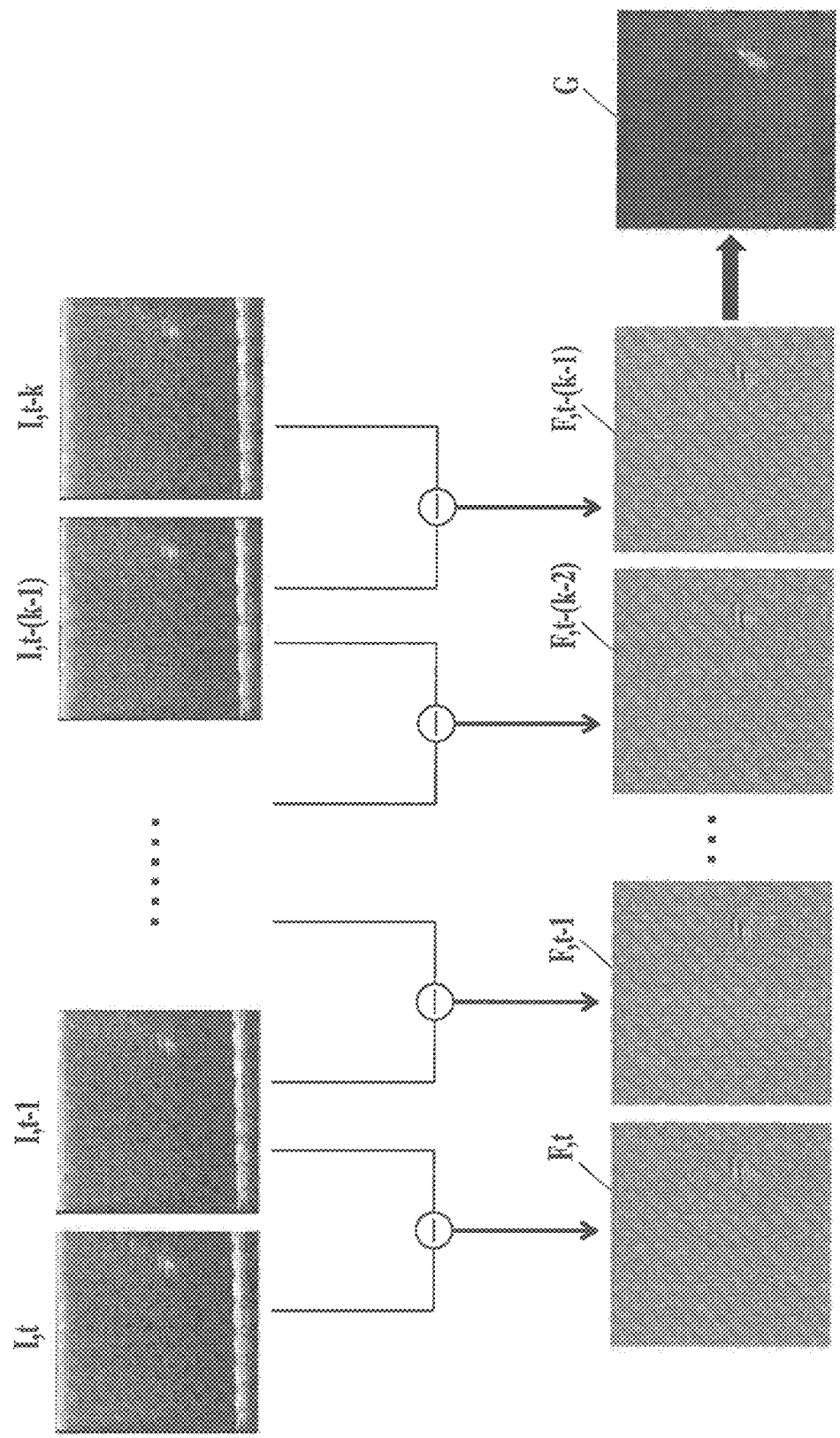
FIG. 7 is a drawing for explaining another example of a generation method of movement evaluation information based on time direction variance.

Here, the method to obtain time direction variance values is not limited to that described above. For example, the same result can be obtained from the method shown in FIG. 7 where differential signals between ultrasound image data of two frames which are consecutive in terms of time, among ultrasound image data of a plurality of frames, are obtained and by analyzing time direction variance of these differential signals to generate movement evaluation information.

In particular, with respect to the differential signal F(t) which expresses differences in the pixels between the ultrasound image data I(t) of the newest frame and the ultrasound image data I(t−1) of the frame which is one frame before the newest frame, the differential signal F(t−1) which expresses the differences in the pixels between the ultrasound image data I(t−1) of the frame which is one frame before the newest frame and the ultrasound image data I(t−2) of the frame which is two frames before the newest frame, . . . , the differential signal F(t−(k−2)) which expresses the differences in the pixels between the ultrasound image data I(t−(k−2)) of the frame which is (k−2) frames before the newest frame and the ultrasound image data I(t−(k−1)) of the frame which is (k−1) frames before the newest frame and the difference signal F(t−(k−1)) which expresses the differences in the pixels between the ultrasound image data I(t−(k−1)) of the frame which is (k−1) frames before the newest frame and the ultrasound image data I(t−k) which is k frames before the newest frame, time direction variance values of differential signals are obtained for individual pixels. For example, with respect to each differential signal, the signal value of a certain coordinates (x, y) is extracted. Then, the average of the extracted signal values is obtained. Thereafter, with respect so the signal value of the coordinates (x, y) in each differential signal, deviation from the average is obtained by the sum of squares. Then, the total sum of the obtained deviations is calculated to obtain the time direction variance value. The greater the variation in values of the differential signals, the greater the time direction variance value is. The time direction variance information G generated as described above is the movement evaluation information.

The puncture needle position detection unit 205c detects the position of the tip of the puncture needle 24 based on the movement evaluation information which is generated by the evaluation information generation unit 205b. As for the detection of the position of the tip of the puncture needle 24, any method described below can be applied, for example.

The first method is detecting a part where the value the movement evaluation information indicates (for example, a differential signal value or a correlation coefficient) fulfills a predetermined condition as the position of the tip of the puncture needle 24. For example, in a case where differential signal values are used as the values the evaluation information indicates, the part where the differential signal value is equal to or greater then a predetermined value is to be detected as the position of the tip of the puncture needle 24. In a case where correlation coefficients are used as the values the evaluation information indicates, the part where the correlation coefficient is equal to or smaller than a predetermined value is to be detected as the position of the tip of the puncture needle 24. In such way, the position of the tip of the puncture needle 24 can be detected in a simple method. However, there are cases where a plurality of positions are detected as the tip of the puncture needle due to the influence of body movement, noise, etc. in such cases, detection accuracy can be enhanced by the following methods.

The second method is detecting the tip of the puncture needle 24 based on the movement evaluation information within a region which is a predetermined range from the position of the tip of the puncture needle 24 detected in the ultrasound image data of a past frame (for example, one frame before). The position information of the tip of the puncture needle 24 detected in the ultrasound image data of a past frame can be obtained from the history information relating to the position of the tip of the puncture needle 24 stored in the history storage unit 205d. According to this, a position distant from the actual puncture needle 24 can be avoided from being detected as the tip of the puncture needle, and therefore, detection accuracy can be enhanced.

Figure 8:
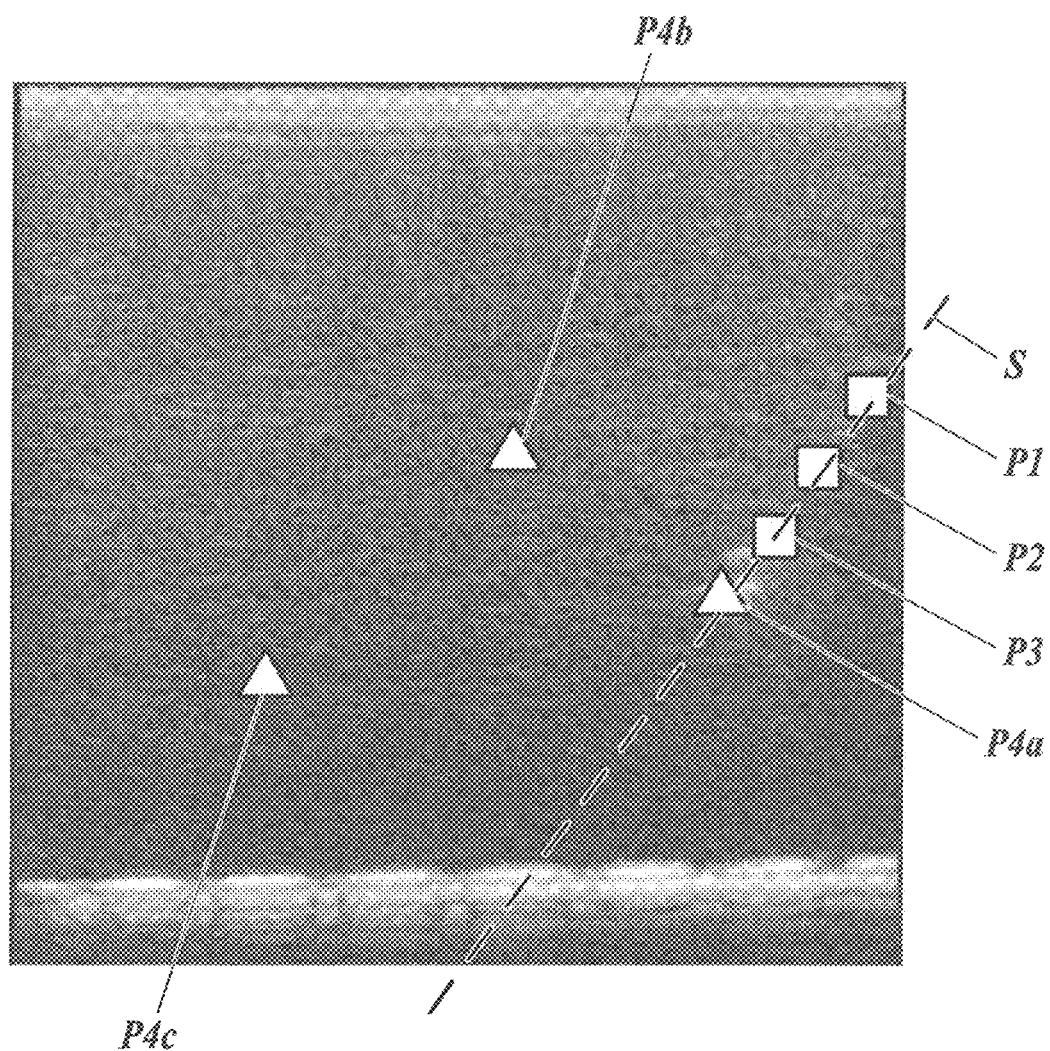
FIG. 8 is a drawing for explaining a method to detect the tip of a puncture needle based on history information.

The third method is obtaining the straight-line trajectory of the tip of the puncture needle 24 based on the history information relating to the position of the tip of the puncture needle 24 stored in the history storage unit 205d in an after-mentioned manner and detecting the tip of the puncture needle 24 based on the values the movement evaluation information indicates at the periphery of the straight-line trajectory. For example, the straight-line trajectory can be obtained by the least squares line. More specifically, for example, when the points P1 to P3 represent the detection positions of the puncture needle 24 in the ultrasound image data of a past frame according to the history information as shown in FIG. 8, the least squares line is calculated from these detection positions P1 to P3 to obtain the straight-line trajectory S. When there are a plurality of points whose values the movement evaluation information indicates are equal to or greater than a predetermined value (P4a, P4b, P4c), since the point P4a among these points is at the periphery of the straight-line trajectory S, the point P4a is to be detected as the tip of the puncture needle 24.

The fourth method is detecting the position of the tip of the puncture needle 24 based on the movement evaluation information generated as described above by using a particle filter. Hereinafter, the fourth method will be described in detail with reference to FIG. 9.

Figure 9:
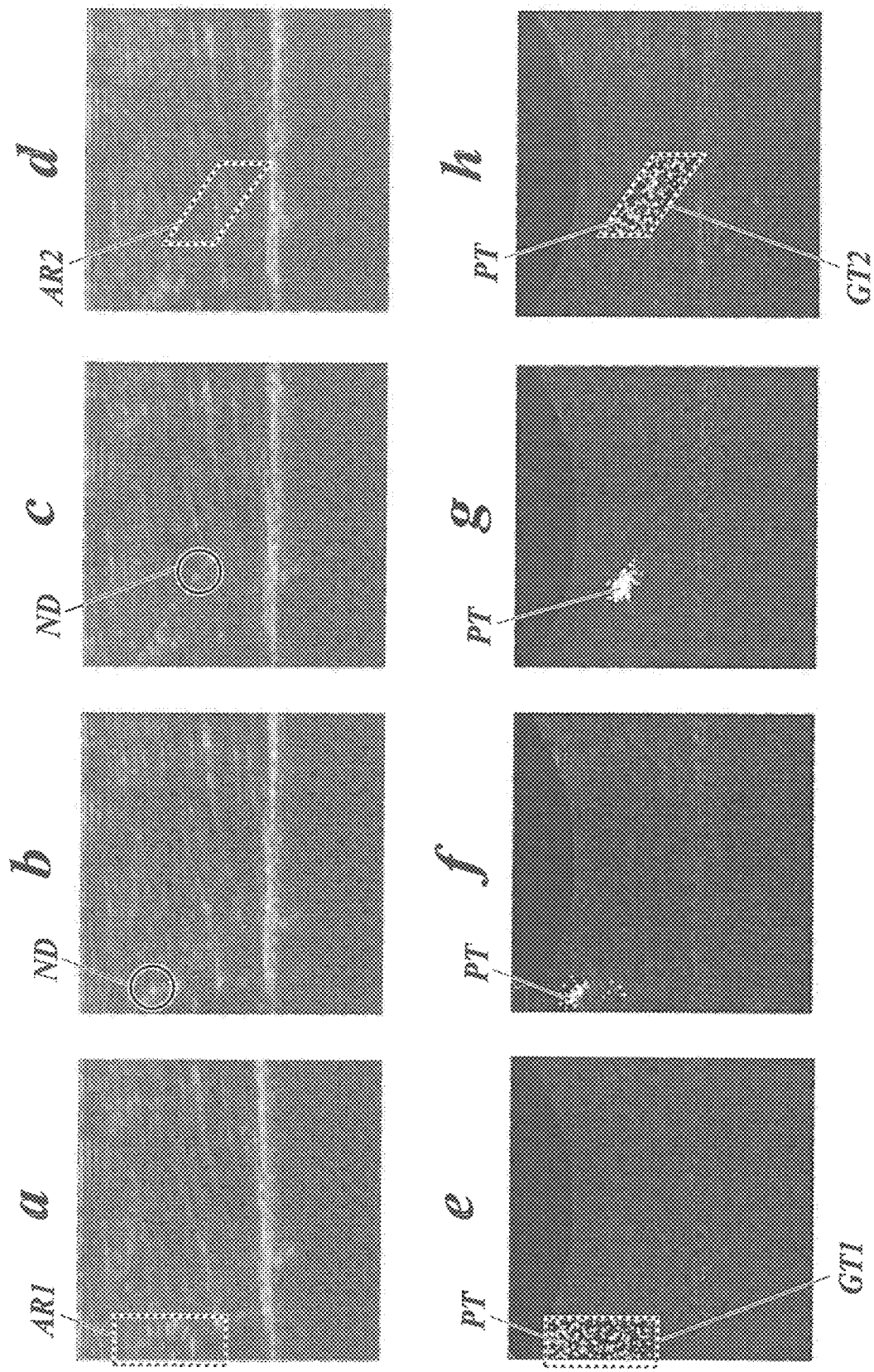
FIG. 9 is a drawing for explaining a method to detect the position of the tip of a puncture needle by using a particle filter.

The image "a" of FIG. 9 shows the ultrasound image before the puncture needle 24 is inserted. The image "e" of FIG. 9 shows the movement evaluation information generated based on the differential signals between the ultrasound image data according to the ultrasound image which is the image "a" of FIG. 9 and the ultrasound image data obtained from the frame which is one frame before. Here, the movement evaluation information generated based on correlation coefficients instead of differential signals may be applied.

First, with respect to the region in the movement evaluation information shown in the image "e" of FIG. 9 corresponding to the puncture needle inserting region AR1 shown in the image "a" of FIG. 9, initialization for setting the needle signal detection gate GT1 where number of particles PT are uniformly arranged is performed. The needle signal detection gate GT1 is a filter for detecting insertion of the puncture needle 24 in the puncture needle inserting region AR1 with good accuracy. In the embodiment, only one needle signal detection gate GT1 is provided at the left side. However, the arrangement position is not limited to this, and it is preferred that the needle signal detection gate GT1 is arranged at the position where the puncture needle 24 is likely to be inserted. Further, the needle signal detection gate GT1 does not need to be provided.

Next, prediction processing wherein the individual particles PT are moved on the basis of a predetermined state transition model, is performed. The state transition model is a rough movement of the puncture needle 24, for example.

Next, observation processing wherein a rectangle is formed for each particle PT and a pixel value of inside the formed rectangle is obtained is performed.

Figure 10:
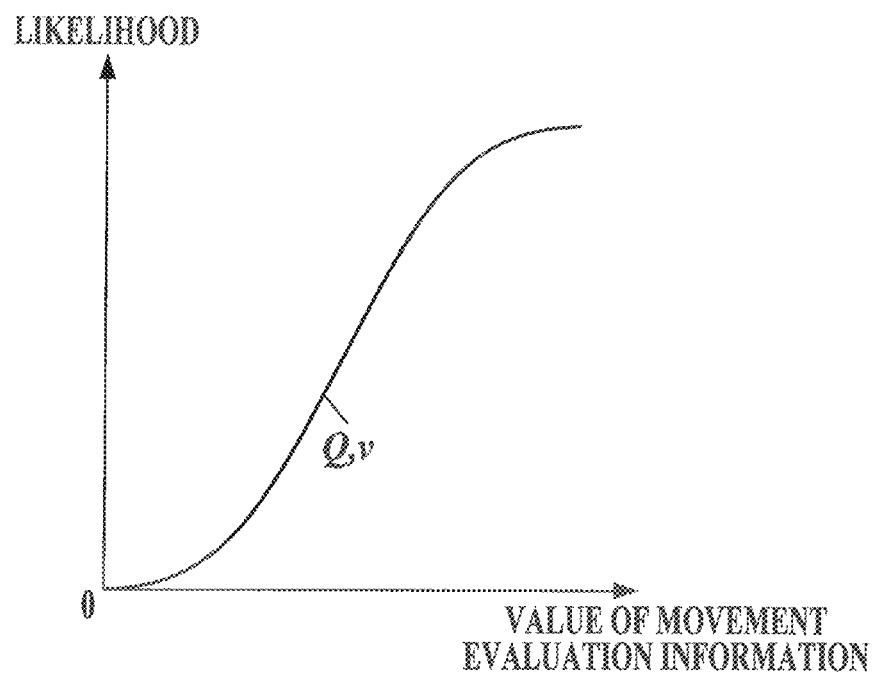
FIG. 10 is a drawing for explaining a likelihood function.

Next, likelihood calculation processing wherein the likelihood is calculated for each particle PT and the weight is obtained from the calculated likelihood is performed. Likelihood is obtained by comparing the pixel value estimated from she state of she particle PT to the pixel value obtained by the observation processing and likelihood indicates the likelihood of the estimated pixel value to the pixel value obtained by the observation processing. For example, likelihood can be obtained from a value the movement evaluation information indicates by using the likelihood function Q(v) as shown in FIG. 10.

Next, a weighted average is obtained, the likelihood of individual particles PT calculated by she likelihood calculation processing being the weights. Then, whether the weighted average is equal to or greater than a predetermined threshold is determined. If the weighted average is not equal to or greater than the threshold, this is interpreted that insertion of the puncture needle 24 is not detected, and the initialization processing is executed in the state where the needle signal detection gate GT1 as set.

On the other hand, when the puncture needle 24 is inserted and the puncture needle image ND appears in the ultrasound image as shown in the image "b" of FIG. 9, the weighted average is to be equal to or greater than the threshold. In such case, target estimation processing wherein the setting of the needle signal detection gate GT1 is resolved and the barycentric coordinates of the particles Pt is obtained to estimate the center position of the tip of the puncture needle 24 as the target object is performed. The barycentric coordinates of the particles Pt is stored as history.

Next, selection processing wherein the particles PT having high likelihood are generated more, statistically, and the particles PT having low likelihood are eliminated on the basis of the likelihood of individual particles PT. Then, as shown in the image "f" of FIG. 9, the particles PT having high likelihood are readily selected and thus, a number of particles PT gather together. Thereafter, by repeating the above described processing, when the puncture needle image ND moves as shown in the image "c" of FIG. 9, the gathered group of particles PT follows the movement as shown in the image "g" of FIG. 9.

Thereafter, when she puncture needle 24 stops in the subject and the puncture needle 24 cannot be detected based on the movement evaluation information, the rectangular needle signal detection gate GT2 is set again at the region in the movement evaluation information shown in the image "h" of FIG. 9 corresponding to the puncture needle existence estimated region AR2 having the position estimated as the position where the tip of the puncture needle 24 stopped as the center thereof as shown in the image "d" of FIG. 9. For example, the shape and position of the needle signal detection gate GT2 are set based on the history of barycenter coordinates of the particles PT. In particular, since the moving direction and position of she puncture needle image ND can be estimated from the history of barycenter coordinates of the particles PT, the center position of the needle signal detection gate GT2 and the inclination of its shape can be obtained. Further, the width of the needle signal detection gate GT2 may be set based on the moving speed of the puncture needle image ND which is calculated from the history of barycenter coordinates of the particles PT. In such way, when the puncture needle 24 moves again, the moving can be detected with good accuracy.

In the embodiment, the most recent plurality (for example, 5 points) of barycenter coordinates are extracted from the history of barycenter coordinates of the particles PT and an approximation straight line can be obtained based on these barycenter coordinates. For example, the approximation straight line can be obtained by the least squares line. Then, the correlation coefficients between the approximation straight line and the plurality of barycenter coordinates are obtained and whether the correlation is high is determined. When the correlation is high, insertion information such as the insertion angle of the puncture needle 24, the depth of the tip of the puncture needle 24, etc. is stored so that such information can be displayed in the display unit 207, for example.

The fifth method is obtaining the moving amount of the tip of the puncture needle 24 from its position detected in the ultrasound image data of a past frame (for example, one frame before) by using the moving speed of the tip of the puncture needle 24 which is calculated by the speed calculation unit 205*e*, and detecting the tip of the puncture needle 24 based on the values the movement evaluation information indicates in the region which is estimated from the moving amount. In addition to moving speed of the tip of the puncture needle 24, its acceleration may be calculated, and the moving amount of the tip of the puncture needle 24 can be obtained based on the moving speed and acceleration. More in particular, for example, in a case where the points P1 to P3 are the detection positions of the puncture needle 24 in the ultrasound image data of a past frame according to the history information as shown in FIG. 8, the speed calculation unit 205*e* calculates the moving speed of the puncture needle 24 between the point P1 and the point P2 based on the moving amount of the puncture needle 24 from the point P1 to the point P2 and calculates the moving speed of the puncture needle 24 between the point P2 and the point P3 based on the moving amount of the puncture needle 24 from the point P2 to the point P3. Then, the acceleration is calculated from the difference between the above calculated moving speeds. The puncture needle position detection unit 205*c* calculates the moving amount of the tip of the puncture needle 24 from the point P3 based on the moving speed and acceleration of the puncture needle 24 between the point P2 and the point P3. In a case where there are a plurality of points (P4*a*, P4*b*, P4*c*) whose values the movement, evaluation information indicates are equal to or greater than a predetermined value, among these points, the point P4*a* is at the position distant from the point P3 by the calculated moving amount. Therefore, the point P4*a* is to be detected as the tip of the puncture needle 24. In such way, the moving destination of the tip of the puncture needle 24 can be estimated with good accuracy. Therefore, detection accuracy of the tip of the puncture needle 24 can be enhanced. Here, by combining the fifth method with the above described first to fourth methods, detection accuracy of the tip of the puncture needle 24 can be enhanced even more.

The sixth method is detecting, on the basis of the moving amount of the tip of the puncture needle 24 in a past frame (for example, one frame before), the tip of the puncture needle 24 based on the value the movement evaluation information indicates at the position distant from the position of the tip of the puncture needle 24 detected in the ultrasound image data of the past frame by the moving amount. In such case, for example, the moving amount can be obtained by the optical flow. In such method, since the detection range changes according to the moving amount (moving speed) of the puncture needle 24, detection can be performed taking the moving speed of the tip of the puncture needle 24 into consideration. Thus, detection accuracy can be enhanced.

In the history storage unit 205*d*, history information relating to the positions of the tip of the puncture needle 24 detected by the puncture needle position detection unit 205*c* is stored.

The speed calculation unit 205*e* calculates the moving speed of the puncture needle 24 on the basis of the history information relating to the positions of the tip of the puncture needle 24 stored in the history storage unit 205*d* as described above.

The highlighting unit 205*f* performs correction of ultrasound image data so as to highlight the display of the tip image in the ultrasound image, the tip image corresponding to the position of the tip of the puncture needle 24 detected by the puncture needle position detection unit 205*c*.

Figure 11:
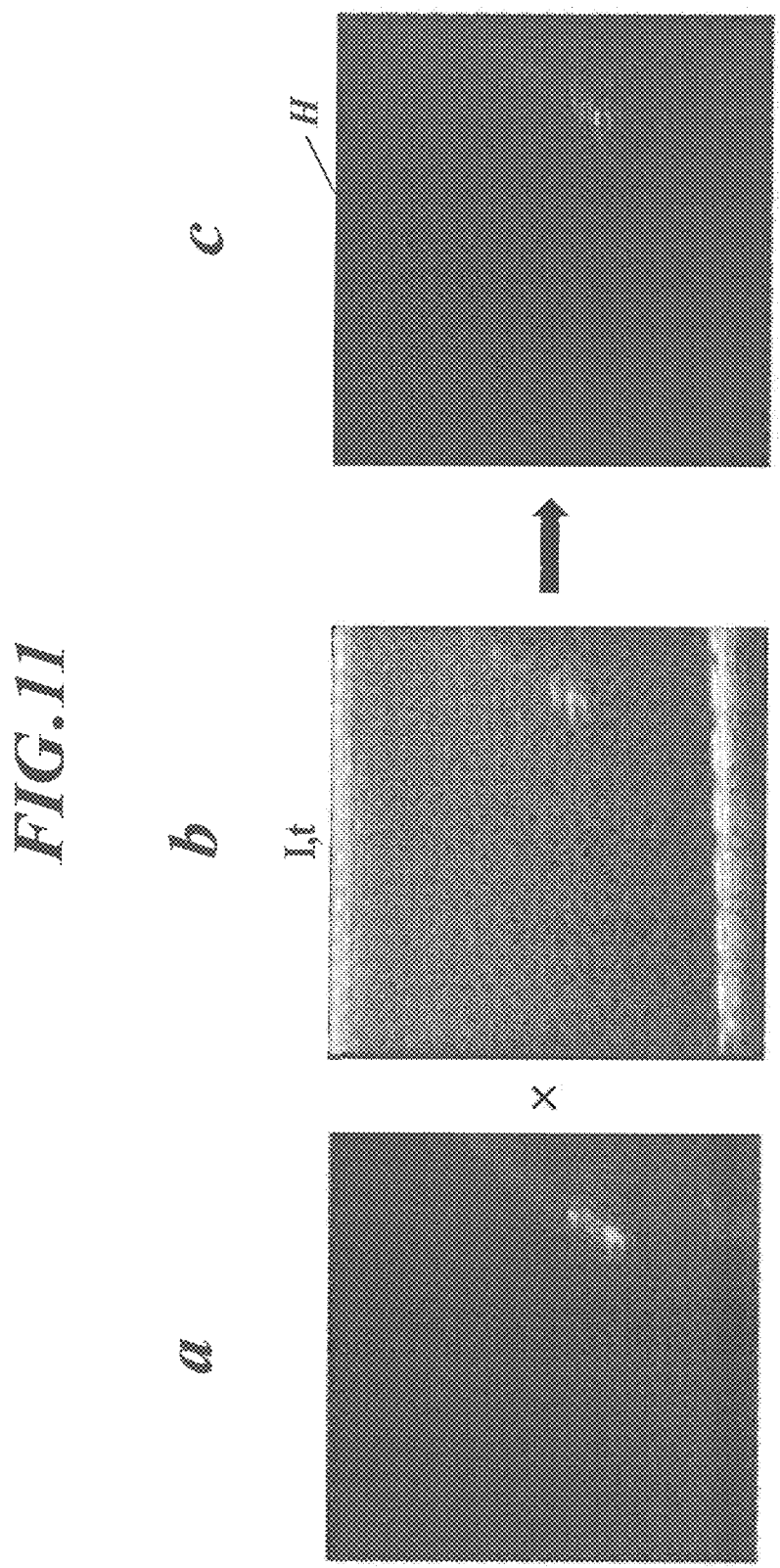
FIG. 11 is a drawing for explaining an image showing the tip of a puncture needle.
Figure 12:
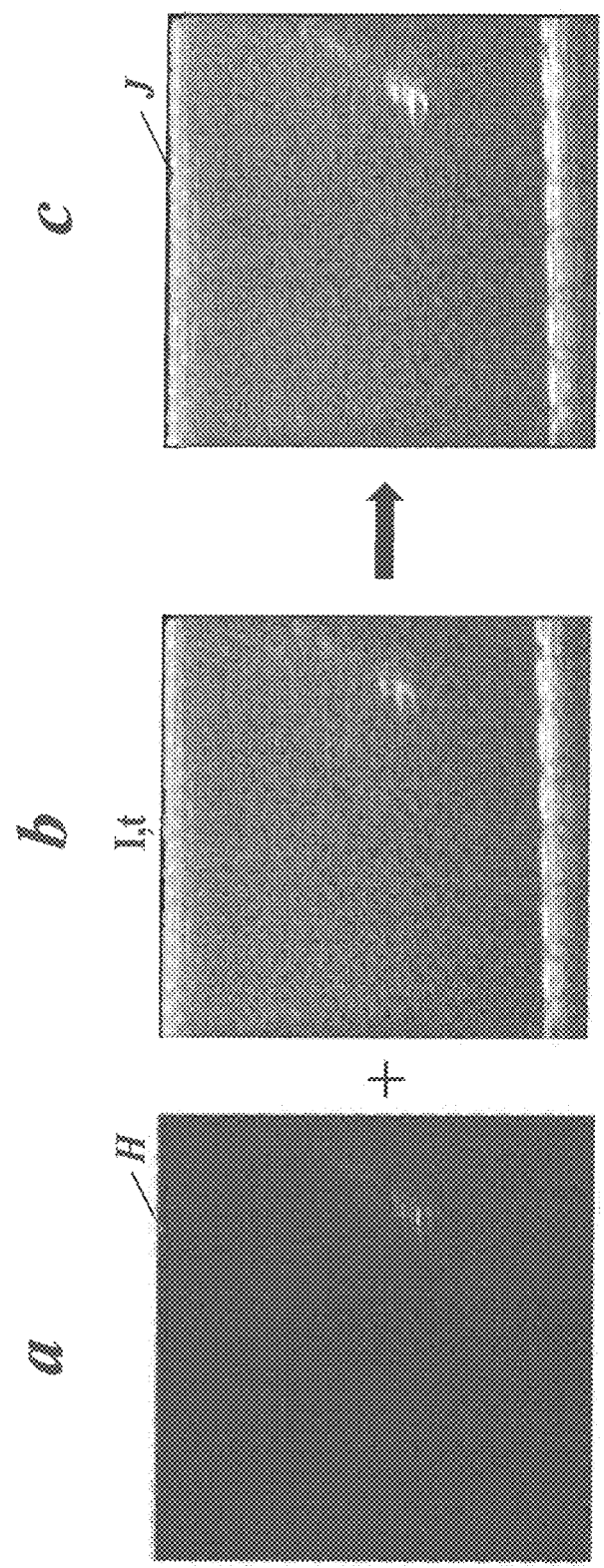
FIG. 12 is a drawing for explaining highlighting display of the tip of a puncture needle.

In particular, first, with respect to the movement evaluation information generated as described above, filtering is performed on the part other than the position where the tip of the puncture needle 24 is detected on the basis of the detection information of the position of the tip of the puncture needle 24 obtained, by the puncture needle position detection unit 205*c*. Then, the movement evaluation information on which the filtering is performed is converted into a puncture needle tip signal highlighting coefficient as shown in the image "a" of FIG. 11 by using a table such as a LUT (Look Up Table), for example. Thereafter, the ultrasound image data I(t) of the newest frame as shown in the image "b" of FIG. 11 is multiplied by the puncture needle tip signal highlighting coefficient to obtain image data of the image H (puncture needle tip image) showing the puncture needle tip as shown in the image "c" of FIG. 11. Further, the image data of the puncture needle tip image. H shown in the image. "a" of FIG. 12 is added to the ultrasound image data I(t) of the newest frame shown in the image "b" of FIG. 12 to generate image data of the ultrasound image J wherein the tip of the puncture needle is highlighted as shown in the image "c" of FIG. 12.

In the embodiment, when highlighting the tip of the puncture needle by increasing the brightness of the tip portion of the puncture needle, the degree of highlighting can be changed according to the moving speed of the tip of the puncture needle. For example, the degree of highlighting may be made to be low while the puncture needle is moving and the degree of highlighting may be made to be high while the puncture needle is not moving. In such way, behavior of the puncture needle 24 can be recognized and the tip of the puncture needle 24 can be recognized easier.

Highlighting of the tip of the puncture needle may be performed by changing the display color of the puncture needle tip portion. The display color may be changed according to the moving speed of the tip of the puncture needle. For example, the tip of the puncture needle may be displayed in red while the puncture needle is moving and the tip of the puncture needle may be displayed in blue when the puncture needle is not moving.

The trajectory display unit 205*g* controls so as to display the trajectory of the tip of the puncture needle 24 on the basis of the history information relating to the position of the tip of the puncture needle 24 stored in the history storage unit 205*d*. In particular, history of a plurality of positions is extracted from the history information of the position of the tip of the puncture needle 24 stored in the history storage unit 205*d*, and a moving trajectory is calculated by the least she squares line, for example, on the basis of the extracted history of positions. Then, the trajectory display unit 205*g* combines the ultrasound image data and the data showing the moving trajectory so that the calculated moving trajectory is to be displayed in the ultrasound image. In such way, the moving destination of the tip of the puncture needle 24 can be predicted. Therefore, the tip of the puncture needle 24 can be recognized easier. Here, the moving trajectory may not be displayed according to the operation of the operation input unit 201. Further, the configuration may be without the trajectory display unit 205*g*.

As shown in FIG. 2, the DSC 206 converts ultrasound image data received from the image processing unit 205 into an image signal of television signal scanning method and outputs the image signal to the display unit 207.

As for the display unit 207, display apparatuses such as a LCD (Liquid Crystal Display), a CRT (Cathode-Ray Tube) display, an organic EL (Electronic Luminescence) display, an inorganic EL display or a plasma display can be applied.

The display unit 207 displays an ultrasound image on the display screen according to the image signal output from the DSC 206.

The control unit 208 includes a CPU (Central Processing Unit), a ROM (Read Only Memory) and a RAM (Random Access Memory), for example. The control unit 208 reads out various types of programs such as a system program stored in the ROM and opens them in the RAM and collectively controls the operations of the components in the ultrasound diagnostic imaging apparatus 20 in compliance with the opened programs.

The ROM is configured of a non-volatile memory of semiconductor or the like, and stores a system program corresponding to the ultrasound diagnostic imaging apparatus 20, various types of processing programs which can be executed on the system program, various types of data and the like. These programs are stored in the forms of program codes which can be read by a computer and the CPU sequentially executes the operations according to the program codes.

The RAM forms a work area in which various types of programs to be executed by the CPU and data relating to these programs are to be stored temporarily.

Figure 13:
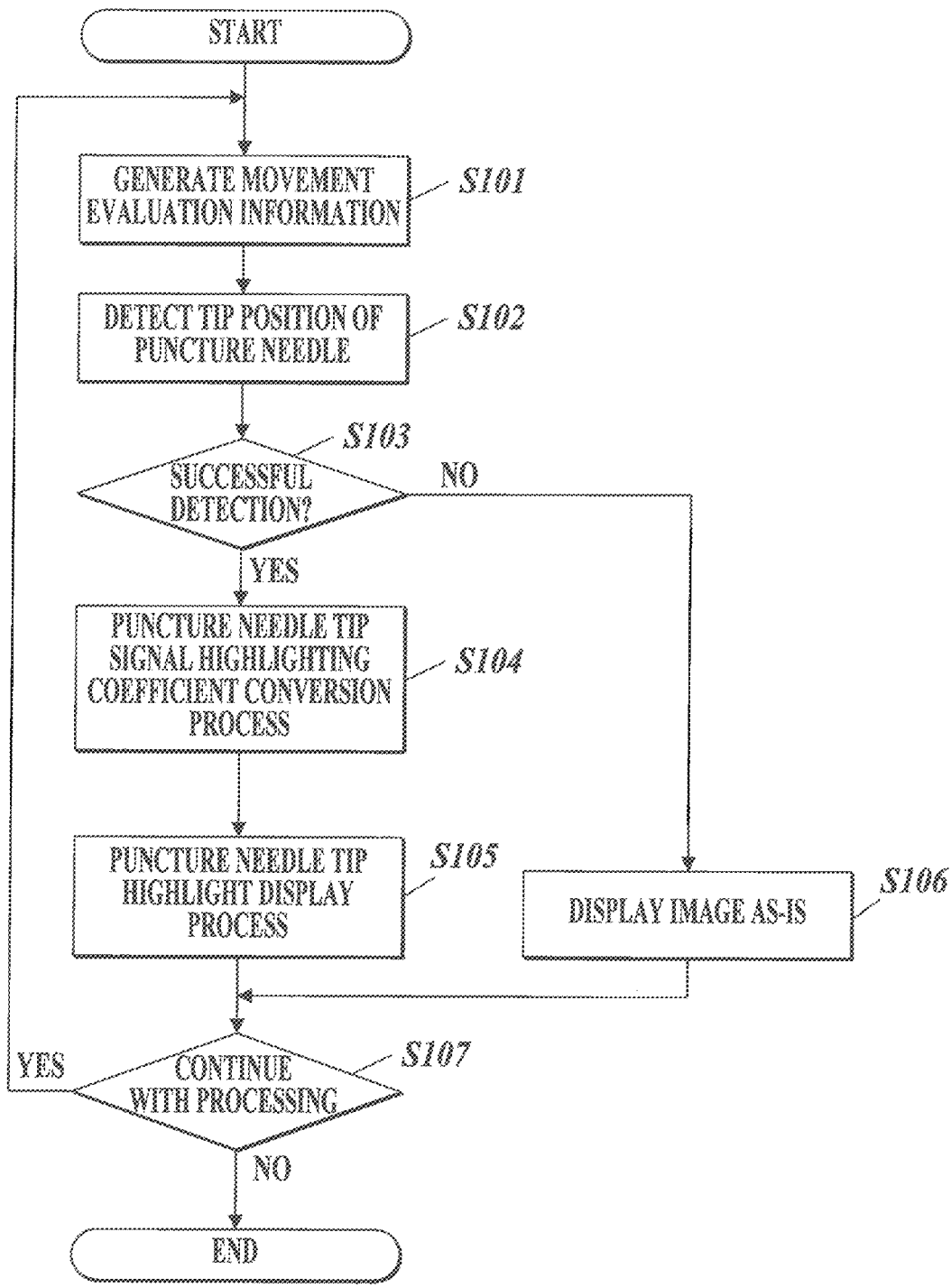
FIG. 13 is a flowchart for explaining an image data generation process.

Next, an example of image data generation processing which is executed by the control unit 208 of the ultrasound diagnostic imaging apparatus 20 configured as described above will be described with reference to FIG. 13. The image data generation processing is executed according to a predetermined examination start operation performed by an operator such as a physician, a medical technologist, etc.

First, the control unit 208 makes the evaluation information generation unit 205*b* of the image processing unit 205 generate movement evaluation information, and the control unit 208 outputs the generated movement evaluation information to the puncture needle position detection unit 205*c* (step S101).

Next, the control unit 208 detects the position of the tip of the puncture needle 24 on the basis of the movement evaluation information (step S102). In the embodiment, as described, above, history information relating to positions of the tip of the puncture needle 24 is read out from the history storage unit 205*d* and moving speed of the tip of the puncture needle 24 is calculated by the speed calculation unit 205*e* based on the read history information, and based on the result, the position of the tip of the puncture needle 24 can be detected on the basis of the movement evaluation information.

The control unit 208 determines whether the position of the tip of the puncture needle 24 is detected in step S102 (step S103) If it is determined that the position of the tip of the puncture needle 24 is detected (step S103: Y), the control unit 208 makes the highlighting unit 205*f* perform the processing for converting the movement evaluation information into a puncture needle tip signal highlighting coefficient (step S104) and thereafter, the control unit 208 controls so as to generate image data of an ultrasound image wherein the tip of the puncture needle is highlighted and to display an ultrasound image based on the generated ultrasound image data (step S105).

On the other hand, if it is not determined that the position on of the tip of the puncture needle 21 is detected (step S103: N), the control unit 208 controls so that a normal ultrasound image wherein the tip of the puncture needle is not highlighted is displayed (step S106).

The control unit 208 determines whether to continue with the image data generation processing (step S107). That is, the control unit 208 determines whether to continue with displaying of the ultrasound image. If the control unit 208 determines to continue with the image data generation processing (step S107: Y), the control unit 208 executes the processing of step S101. On the other hand, if the control unit 208 does not determined to continue with the image data generation processing (step S107: N), the control unit 208 ends the processing.

Figure 14:
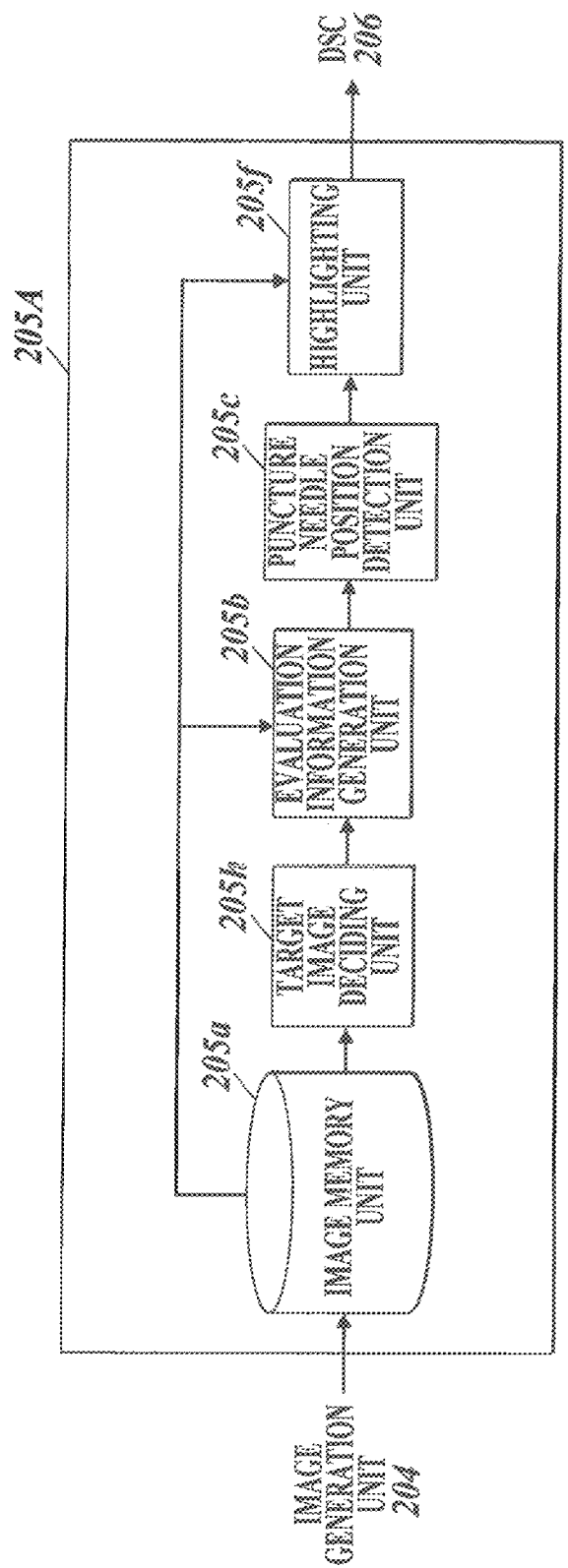
FIG. 14 is a block diagram showing another example of an image processing unit.

Next, another example of the embodiment will be described with reference to FIG. 14. In the example shown in FIG. 14, the image processing unit 205A is different from the image processing unit 205 described above with reference to FIG. 3 in that the image processing unit 205A does not include the history storage unit 205d, the speed calculation unit 205e and the trajectory display unit 205g and includes the target image deciding unit 205h. In the following description, the aspect different from the image processing unit 205 will be described and description of the similar aspects will be omitted.

The target image deciding unit 205h performs global matching of individual ultrasound image data of a plurality of frames stored in the image memory unit 205a to the ultrasound image data of the newest frame to obtain correlations to the ultrasound image data of the newest frame. Then, the target image deciding unit 205h decides the ultrasound image data whose correlation equals to or is greater than a predetermined threshold and which is the oldest in terms of time as the target image data.

Figure 15:
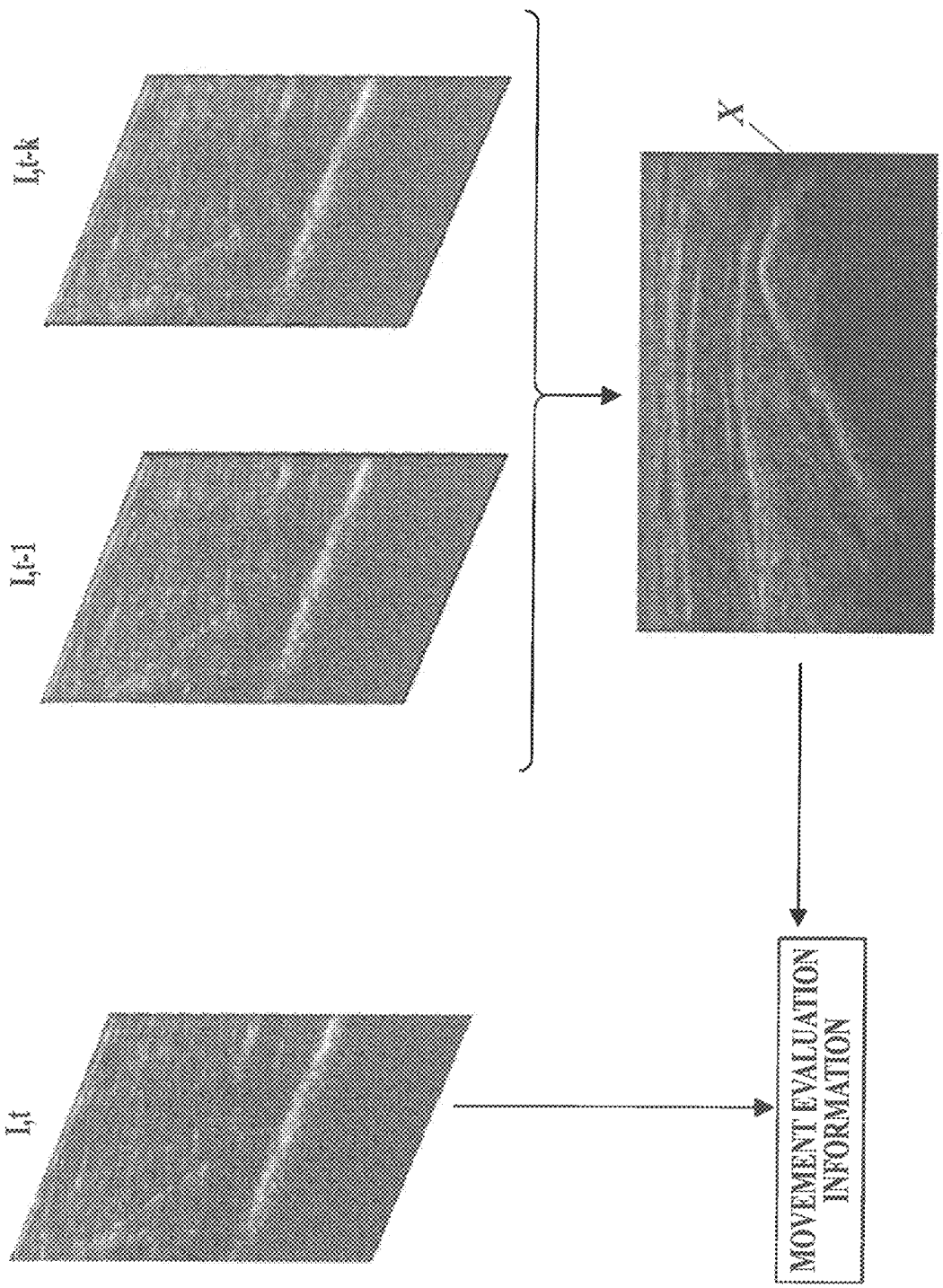
FIG. 15 is a drawing for explaining generation of movement evaluation information.

In particular, for example, global matching is performed between individual ultrasound image data I(t–1) to I(t–k) of frames from the frame which is one frame before the newest frame to the frame which is k frames before the newest frame and the ultrasound image data I(t) of the newest frame to obtain correlations as shown in FIG. 15. In such way, with respect to each of the ultrasound image data I(t–1) to I(t–k), the degree of likeness to the ultrasound image data I(t) of the newest frame can be determined. If the image is greatly changed due to body movement or the like, the degree of likeness is low. Among the ultrasound image data I(t–1) to I(t–k) of frames from the frame which is one frame before the newest frame to the frame which is k frames before the newest frame, the ultrasound image data X whose correlation equals to or is greater than a predetermined threshold and which is the oldest in terms of time is decided as the target image data.

The evaluation information generation unit 205b obtains differential signals or correlation coefficients by the above described procedure based on the ultrasound image data of the target image data which is decided as described above and the ultrasound image data of the newest frame and generates movement evaluation information.

According to the embodiment, movement evaluation information indicating great moving amount of the tip of the puncture needle 24 can be obtained. Therefore, the tip of the puncture needle 24 can be detected easily. Further, since the movement evaluation information is generated by using the ultrasound image data of the newest frame and the ultrasound image data exhibiting a certain level or higher degree of likeness, drop in detection possibilty of the tip of the puncture needle 24 due to the influence of body movement or the like can be reduced.

As described above, according to the embodiment, the ultrasound probe 22 outputs transmission ultrasound toward a subject according to a drive signal, the subject having die puncture needle 24 inserted therein, and outputs a received signal obtained by receiving reflected ultrasound from the subject. The image generation unit 204 and the image processing unit 205 generates ultrasound image data for each frame on the basis of a received signal output from the ultrasound probe 22. The display unit 207 displays an ultrasound image based on the ultrasound image data generated by the image generation unit 204 and the image processing unit 205. The evaluation information generation unit 205b generates movement evaluation information which indicates movement evaluation between frames on the basis of ultrasound image data of a plurality of frames. The puncture needle position detection unit 205c detects the position of the tip of the puncture needle 24 on the basis of the movement evaluation information generated by the evaluation information generation unit 205b. The highlighting unit 205f highlights the display of the tip image in the ultrasound image, the tip image corresponding to the position of the tip of the puncture needle 24 detected by the puncture needle position detection unit 205c. The speed calculation unit 205e calculates moving speed of the tip of the puncture needle 24. The puncture needle position detection unit 205c detects the position of the tip of the puncture needle 24 on the basis of she moving speed of the tip of the puncture needle 24 obtained by the speed calculation unit 205e. As a result, prediction as to where the tip of the puncture needle 24 will move can be made wish good accuracy according to the moving speed of the tip of the puncture needle. Therefore, the tip position of the puncture needle can be figured out accurately.

Further, according to the embodiment, the speed calculation unit 205e calculated acceleration of the tip of the puncture needle 24. The puncture needle position detection unit 205c detects the position of the tip of the puncture needle 24 on the basis of the moving speed and acceleration of the tip of the puncture needle 24 obtained by the speed calculation unit 205e. As a result, prediction as to where the tip of the puncture needle will move can be made with good accuracy according to the moving speed and acceleration of the tip of she puncture needle. Therefore, the tip position of the puncture needle can be figured out accurately.

Furthermore, according to the embodiment, the history storage unit 205d stores history information relating to positions of the puncture needle 24 detected by the puncture needle position detection unit 205c. The speed calculation unit 205e calculates moving speed of the tip of the puncture needle 24 on the basis of the history information relating to positions of the tip of the puncture needle 24 stored in the history storage unit 205d. As a result, there is no effect of body movement, moving of an object other than the puncture needle, noise, etc. on the detection of the tip of the puncture needle, and detection accuracy of the tip of the puncture needle can be more enhanced.

Moreover, according to the embodiment, the evaluation information generation unit 205b generates movement evaluation information by obtaining differential signals between ultrasound image data of a plurality of frames. As a result, movement evaluation information can be generated with a simple method. Therefore, processing load can be reduced.

Further, according to the embodiment, the evaluation information generation unit 205b calculates correlation coefficients between ultrasound image data of a plurality of frames with respect to individual pixels and generates movement evaluation information by obtaining a signal expressing the calculated correlation coefficients of individual pixels. As a result, movement evaluation information that allows good detection of the tip of the puncture needle can be generated.

Furthermore, according to the embodiment, the puncture needle position detection unit 205c detects the position of the tip of the puncture needle 24 within a predetermined range from the position of the tip of the puncture needle 24 detected in the frame which is one frame before. As a result, body movement and an object other than the puncture needle can be prevented from being mistakenly detected as the puncture needle. Therefore, detection accuracy of the tip of the puncture needle can be more enhanced.

Moreover, according to the embodiment, the puncture needle position detection unit 205c obtains the straight-line trajectory of the tip of the puncture needle 24 on the basis of history of the position of the tip of the puncture needle and detects the position of the tip of the puncture needle 24 at the periphery of the straight-line trajectory. As a result, the tip of the puncture needle can be detected while predicting the moving direction of the puncture needle. Therefore, detection accuracy of the tip of the puncture needle can be more enhanced.

Further, according to the embodiment, the puncture needle position detection unit 205c detects the position of the tip of the puncture needle by using a particle filter on the basis of the movement evaluation information generated by the evaluation information generation unit 205b. As a result, by following the tip of the puncture needle, the position of the tip of the puncture needle can be predicted. Therefore, detection accuracy of the tip of the puncture needle can be more enhanced.

Furthermore, according to the embodiment, the highlighting unit 205f increases brightness of the tip image to highlight the tip image in display. As a result, visibility of the tip of the puncture needle can be improved.

Moreover, according to the embodiment, the highlighting unit 205f changes display color of the tip image to highlight the tip image in display. As a result, visibility of the tip of the puncture needle can be improved.

Further, according to the embodiment, the trajectory display unit 205g displays the trajectory of the tip of the puncture needle 24 on the basis of history of the position of the tip of the puncture needle 24. As a result, inserting operation of the puncture needle can be performed while predicting the movement of the puncture needle. Therefore, operation accuracy of the puncture needle can be improved.

Furthermore, according to the embodiment, the trajectory display unit 205g obtains the least squares line on the basis of the history of the position of the tip of the puncture needle 24 and displays the trajectory of the tip of the puncture needle 24 on the basis of the least squares line. As a result, movement of the puncture needle can be predicted with great accuracy. Therefore, operation accuracy of the puncture needle can be improved.

Moreover, according to the embodiment, the ultrasound probe 22 outputs transmission ultrasound to a subject according to a drive signal, the puncture needle 24 being inserted in the subject, and outputs a received signal obtained by receiving reflected ultrasound from the subject. The image generation unit 204 and the image processing unit 205 generate ultrasound image data for each frame based on the received signal output from the ultrasound probe 22. The display unit 207 displays an ultrasound image on the basis of the ultrasound image data generated by the image generation unit 204 and the image processing unit 205. The evaluation information generation unit 205b generates movement evaluation information indicating movement evaluation between frames on the basis of ultrasound image data of a plurality of frames. The puncture needle position detection unit 205c detects the position of the tip of the puncture needle 24 on the basis of the movement evaluation information generated by the evaluation information generation unit 205b. The highlighting unit 205f highlights the display of the tip image in the ultrasound image, the tip image corresponding to the position of the tip of the puncture needle 24 detected by the puncture needle position detection unit 205c. The evaluation information generation unit 205b analyzes time direction variance between ultrasound image data of a plurality of frames with respect to individual pixels to generate movement evaluation information. As a result, moving speed of the puncture needle can be recognized easily and movement of the puncture needle can be predicted easily. Therefore, the tip position of the puncture needle can be figured out more accurately.

Further, according to the embodiment, the ultrasound probe 22 outputs transmission ultrasound to a subject according to a drive signal, the puncture needle 24 being inserted in the subject, and outputs a received signal obtained by receiving reflected ultrasound from the subject. The image generation unit 204 and the image processing unit 205A generate ultrasound image data for each frame on the basis of the received signal output from the ultrasound probe 22. The display unit 207 displays an ultrasound image on the basis of the ultrasound image data generated by the image generation unit 204 and the image processing unit 205A. The target image deciding unit 205h performs global matching of individual ultrasound image data of a plurality of frames to the ultrasound image data of the newest frame and obtains correlations of the individual ultrasound image data of a plurality of frames to the ultrasound image data of the newest frame. The target image deciding unit 205h decides the ultrasound image data whose correlation equals to or is greater than a predetermined threshold and which is the oldest in terms of time as the target image data. The evaluation information generation unit 205b generates movement evaluation information indicating movement, evaluation between frames on the basis of the target image data decided by the target image deciding unit 205h and the ultrasound image data of the newest frame. The puncture needle position detection unit 205c detects the position on of the tip of the puncture needle 24 on the basis of the movement evaluation information generated by the evaluation information generation unit 205b. The highlighting unit 205f highlights the display of the tip image in the ultrasound image, the tip image corresponding to the position of the tip of the puncture needle 24 detected by the puncture needle position detection unit 205c. As a result, the movement evaluation information indicating great moving amount of the tip of the puncture needle can be obtained. Therefore, she tip of the puncture needle can be detected easily. Further, since the movement evaluation information is generated by using the ultrasound image data whose likeness to the ultrasound image data of the newest frame equals to or is greater than a certain level. Therefore, drop in detection possibility of the tip of the puncture needle 24 due to the influence of body movement or the like can be reduced.

The Description of the embodiment of the present invention is merely an example of an ultrasound diagnostic imaging apparatus according to the present invention and the present invention is not limited to what is described. The detail configuration and detail operations of the functional parts which constitute the ultrasound diagnostic imaging apparatus can be modified arbitrarily.

In the embodiment, moving speed of the tip of the puncture needle 24 is calculated on the basis of history information relating to the position of the tip of the puncture needle 24 stored in the history storage unit 205d. However, moving speed of the tip of the puncture needle 24 may be calculated on the basis of a plurality of movement evaluation information.

Further, in the embodiment, examples using non-volatile memory of a hard disk or a semiconductor as a computer readable medium of a program according to the present invention is disclosed. However, the configuration of the present invention is not limited to this example. A portable storage medium such as a CD-ROM can be used as another computer readable medium. Further, as a medium for supplying data of a program according to the present invention via a communication wire, carrier wave can also be applied.

The entire disclosure of Japanese Patent Application No 2013-092228 filed on Apr. 25, 2013 is incorporated herein by reference in its entirety.

What is claimed is:

1. An ultrasound diagnostic imaging apparatus, comprising:
    an ultrasound probe which outputs transmission ultrasound to a subject and a puncture needle adapted to be inserted in the subject according to a drive signal, and which outputs a received signal obtained by receiving reflected ultrasound from the subject;
    a memory storing frames of ultrasound image data generated on a basis of received signal output from the ultrasound probe;
    a display which displays an ultrasound image on a basis of the ultrasound image data; and
    a processor configured to:
    perform global matching between individual ultrasound image data of a plurality of the frames and ultrasound image data of a newest frame to obtain correlations of the individual ultrasound image data of the plurality of the frames to the ultrasound image data of the newest frame and determine a target image data to be the individual ultrasound image data of one of the plurality of frames whose correlation equals to or is greater than a predetermined threshold and which is oldest in terms of time;
    generate movement evaluation information indicating movement evaluation between the frames of the ultrasound image data on a basis of the target image data and the ultrasound image data of the newest frame;
    determine a position of a tip of the puncture needle adapted to be inserted in the subject on a basis of the generated movement evaluation information; and
    highlight a tip image in the ultrasound image on the display, the tip image corresponding to the determined position of the tip of the puncture needle.

2. The ultrasound diagnostic imaging apparatus of claim 1, wherein the processor is further configured to calculate a moving speed of the tip of the puncture needle, and determine the position of the tip of the puncture needle in the newest frame of the ultrasound image data on a basis of the moving speed of the tip of the puncture needle.

3. The ultrasound diagnostic imaging apparatus of claim 2, wherein the processor is configured to calculate an acceleration of the tip of the puncture needle based on the ultrasound image data of the plurality of the frames and the ultrasound image data of the newest frame, and wherein the position of the tip of the puncture needle is determined on a basis of the moving speed and the acceleration of the tip of the puncture needle.

4. The ultrasound diagnostic imaging apparatus of claim 2, wherein the memory stores history information relating to the position of the tip of the puncture needle in at least one past frame, wherein the processor calculates moving speed of the tip of the puncture needle on a basis of the history information relating to the position of the tip of the puncture needle stored in the memory and the frame rate.

5. The ultrasound diagnostic imaging apparatus of claim 2, wherein the processor generates the movement evaluation information by obtaining differential signals between the ultrasound image data of the plurality of frames.

6. The ultrasound diagnostic imaging apparatus of claim 2, wherein the processor calculates correlation coefficients between the ultrasound image data of the plurality of frames with respect to individual pixels and generates the movement evaluation information by obtaining a signal expressing the calculated correlation coefficients of the individual pixels.

7. The ultrasound diagnostic imaging apparatus of claim 2, wherein the processor generates the movement evaluation information by analyzing time direction variance between the ultrasound image data of the plurality of frames with respect to individual pixels.

8. The ultrasound diagnostic imaging apparatus of claim 2, wherein the processor detects a position of the tip of the puncture needle in the newest frame within a predetermined range from the position of the tip of the puncture needle detected in a frame which is a most recent frame before the newest frame.

9. The ultrasound diagnostic imaging apparatus of claim 2, wherein the processor obtains a straight line trajectory of the tip of the puncture needle on a basis of position history of the tip of the puncture needle and detects the position of the tip of the puncture needle at a predetermined area along the straight line trajectory.

10. The ultrasound diagnostic imaging apparatus of claim 2, wherein the processor detects the position of the tip of the puncture needle on a basis of the movement evaluation information generated by using a particle filter.

11. The ultrasound diagnostic imaging apparatus of claim 2, wherein the processor highlights the display of the tip image by increasing brightness of the tip image.

12. The ultrasound diagnostic imaging apparatus of claim 2, wherein the processor highlights the display of the tip image by changing a display color of the tip image.

13. The ultrasound diagnostic imaging apparatus of claim 2, wherein the processor is further configured to display a trajectory of the tip of the puncture needle on a basis of position history of the tip of the puncture needle.

14. The ultrasound diagnostic imaging apparatus of claim 13, wherein the processor obtains a least squares line on a basis of the position history of the tip of the puncture needle and displays the trajectory of the tip of the puncture needle on a basis of the least squares line.

* * * * *